(12) United States Patent
Wikberg et al.

(10) Patent No.: US 6,599,943 B1
(45) Date of Patent: Jul. 29, 2003

(54) USE OF HYDROXYGUANIDINES

(75) Inventors: Jarl Wikberg, Sigtuna (SE); Peteris Prusis, Uppsala (SE); Maija Dambrova, Uppsala (SE); Staffan Uhlén, Uppsala (SE)

(73) Assignee: WaPharm AB, Uppsala (SE)

( * ) Notice: Subject to any disclaimer, the term of this patent is extended or adjusted under 35 U.S.C. 154(b) by 0 days.

(21) Appl. No.: 09/318,848

(22) Filed: May 26, 1999

Related U.S. Application Data

(63) Continuation of application No. PCT/SE97/01969, filed on Nov. 21, 1997, now abandoned.

(30) Foreign Application Priority Data

Nov. 26, 1996 (SE) .............................................. 9604348

(51) Int. Cl.⁷ ............................................ A61K 31/155
(52) U.S. Cl. ...................................................... 514/634
(58) Field of Search ......................................... 514/634

(56) References Cited

U.S. PATENT DOCUMENTS

| | | | |
|---|---|---|---|
| 3,591,636 A | 7/1971 | Houlihan et al. | 260/564 |
| 3,592,852 A | 7/1971 | Houlihan et al. | 260/564 |
| 3,867,447 A | 2/1975 | Cherkofsky | 260/564 G |
| 4,006,250 A | 2/1977 | Childress | 424/326 |

FOREIGN PATENT DOCUMENTS

GB 1223491 2/1971

OTHER PUBLICATIONS

Chevallet, P. et al., "Synthese d'aryloxyacétaldéhyde N'–hydroxyganylhydrazones," *Bull. Soc. Chim. Fr.* pp. 81–86 (Jan.–Feb. 1991).

Abstract of Chevallet, P. et al., "Synthesis of aryloxyacetaldehyde N'–hydroxyguanylhydrazones," *Bull. Soc. Chim. Fr.* pp. 81–86 (Jan.–Feb. 1991), STN International, File CAPLUS, CAPLUS Accession No. 1991:448808.

Clement, B. et al., "Microsomal Catalyzed N–Hydroxylation of Guanabenz and Reduction of the N–Hydroxylated Metabolite: Characterization of the Two Reactions and Genotoxic Potential of Guanoxabenz," *Chem. Res. Toxicol.* 9:682–688 (Jun. 1996).

Abstract of Clement, B. et al., "Microsomal Catalyzed N–Hydroxylation of Guanabenz and Reduction of the N–Hydroxylated Metabolite: Characterization of the Two Reactions and Genotoxic Potential of Guanoxabenz," *Chem. Res. Toxicol.* 9:682–688 (Jun. 1996) STN International, File CAPLUS, CAPLUS, Accession No. 1996:287980.

Kokkinidis, G. et al., "sue of Pt/M(UPD) (M=Pb, Tl, Bi) Modified Electrodes to the Catalytic Electroreduction of Heterocyclic Nitro Compounds–I. 3–Nitro–1H–1,2,4–Triazole," *Electrochim. Acta* 35:1957–1964 (1990).

Abstract of Kokkinidis, G. et al., "Use of platinum/metal (underpotential deposited) (metal = lead, thallium, bismuth) modified electrodes to the catalytic electroreduction of heterocyclic nitro compounds. I. 3–Nitro–1H–1,2,4–triazole," *Electrochim. Acta* 35:1957–1964 (1990), STN International, File CAPLUS, CAPLUS Accession No. 1991:90550.

Pandey, C. et al., "Quantitative structure–activity relationship studies on some anticancerous, antiviral and cytostatic agents," *Indian J. Biochem. Biophys.* 26:405–409 (Dec. 1989).

Wang, P.H. et al., "Quantitative structure–activity relationship (QSAR) analysis of the cytotoxicities of aminohydroxyguanidine derivatives and their antiviral activities in vitro," *Pharm. Res.* 8:1006–1012 (Aug. 1991).

Abstract of Wang, P.H. et al., "Quantitative Structure–activity Relationship (Qsar) Analysis of the Cytotoxicities of Aminohydroxyguanidine Derivatives and Their Antiviral Activities in Vitro," *Phrm. Res.* 8:1006–1012 (Aug. 1991). STN International, File CAPLUS, CAPLUS Accession No.1992:50862.

International Search Report for International Application No. PCT/SE97/01969, mailed Mar. 4, 1998.

Tai, A.W., et al., "Novel N–Hydroxyguanidine Derivatives as Anticancer and Antiviral Agents", *J. Med. Chem.* 27:236–238 (1984).

Dambrova, M., et al., "N–Hydroxyguanidine Compound PR5 Inhibits the Xanthine Oxidase–Mediated Generation of Superoxide Radical,"*Arch. Biochem. Biophys.* 377:101–108, Academic Press, Inc. (May 2000).

Dambrova, M., et al., Characterization of the Enzymatic Activity for Biphasic Competition by Guanoxabenz (1–(2, 6–dichlorobenzylidene–amino)–3–hydroxyguanidine) at $\alpha_2$–Adrenoceptors II. *Biochem. Pharmacol.* 56:1121–1128, Elsevier (Nov. 1998).

Dambrova, M., et al., "Characterization of Guanoxabenz Reducing Activity in Rat Brain," *Pharmacol. and Toxicol.* 83:158–163, Munksgaard International Publishers (Oct. 1998).

Dambrova, M., et al., "Identification of an N–hydroxyguanidine reducing activity of xantine oxidase,"*Eur. J. Biochem.* 257:178–184, Springer (Oct. 1998).

Uhlé, S., et al., Characterization of the Enzymatic Activity for Biphasic Competition by Guanoxabenz (1–(2, 6–dichlorobenzylidene–amino)–3–hydroxyguanidine) at $\alpha_2$–Adrenoceptors I. Biochem. Pharmacol. 56:1111–1119, Elsevier (Nov. 1998).

Veveris, M., et al., "Cardioprotective effects of N–hydroxyguanidine PR5 in myocardial ischemic and reperfusion in rats," *Br. J. Pharmacol.* 128:1089–1097, MacMillan Journals (Nov. 1999).

Wiksberg, J.E.S., et al., "Conditions for Biphasic Competition Curves in Radioligand Binding for Ligands Subjected to Metabolic Transformation," *Biochem. Pharmacol.* 56:1129–1137, Elsevier (Nov. 1998).

*Primary Examiner*—Raymond Henley, III
(74) *Attorney, Agent, or Firm*—Sterne, Kessler, Goldstein & Fox P.L.L.C.

(57) ABSTRACT

The invention features pharmaceutical compositions that include hydroxyguanidines. The compositions can be used, for example, for treating or preventing ischemic diseases, hypoxia,or arrhythmias.

12 Claims, 8 Drawing Sheets

Accumulation of guanabenz during incubation of guanoxabenz with spleen cytosol

NMR spectroscopy of guanabenz (A), guanaoxabenz (B), and the HPLC purified product formed upon incubation of guanoxabenz with spleen cytosol (C)

Radioligand binding assay of hydroxyguanidine reducing activity

Radioligand binding assay of
hydroxyguanidine reducing activity
of bovine xanthine oxidase Oxidation of xanthine to uric acid by bovine xanthine oxidase Inhibition of xanthine oxidase promoted superoxide radical formation by guanoxabenz. EPR spectra.

Oxidation of xanthine to uric acid sustained by hydroxyguanidines

Inhibition of hydroxyguanidine reducing activity
of bovine xanthine oxidase by allopurinol.
Radioligand binding assay

USE OF HYDROXYGUANIDINES

CROSS-REFERENCE TO RELATED APPLICATIONS

This is a continuation of International Application PCT/SE97/01969, which has an International filing date of Nov. 21, 1997, now abandoned.

FIELD OF THE INVENTION

The present invention relates to the use of hydroxyguanidines in the prevention and treatment of a variety of diseases as well as to the protection of organs intended for transplantation. The present invention also relates to pharmaceutical compositions containing hydroxyguanidines intended for such use. Furthermore the invention relates to the manufacture of medicaments containing hydroxyguanidines useful for such prevention and treatment.

BACKGROUND OF THE INVENTION

Xanthine dehydrogenase (EC 1.1.1.204) and xanthine oxidase (EC 1.1.3.22) are closely related molybdenum, iron-sulphur and flavin containing enzymes that catalyze the oxidation of purines such as hypoxanthine and xanthine leading to formation of, respectively, xanthine and uric acid (Pritsos & Gustafson 1994; Hille and Nishino, 1995). It is presumed that xanthine oxidase is formed from the dehydrogenase both in vivo and in vitro by reversible and irreversible postranslational processes. This conversion may occur reversibly by sulfhydryl oxidation, and irreversibly by proteolytic processes (Amaya et al., 1990; Nishino, 1994). The enzymes are composed of two identical subunits of about 1330 amino acids each, which amino acid sequences among mammals are highly conserved (Amaya et al., 1990; Wright et al., 1993; Ichida et al. 1993; Hille and Nishino, 1995). The oxidase and dehydrogenase forms of the enzyme exhibit different reactivities towards molecular oxygen and $NAD^+$, the former oxidant is preferred by the oxidase and the latter by the dehydrogenase (Hille and Nishino, 1995). When oxygen is used as electron acceptor both superoxide radicals (i.e., superoxide anions) and hydrogen peroxide may be generated both of which are considered to be harmful and capable of causing tissue damage (Hille and Nishino, 1995). In particular the oxygen radical is considered to be harmful when present in a living organism, because of its reactivity and the fact that when a radical reacts with a non-radical matter of the organism a new potentially harmful radical is being produced (Kooij, 1994). The superoxide radical may react with $H^+$ under formation of the perhydroxyl radical $HO_2$. which is capable to react substantially faster than superoxide with tissue components (Kooji, 1994). Moreover, the perhydroxyl radical may form hydrogen peroxide which also may disintegrate to the extremely reactive hydroxyl radical .OH (Xia et al., 1996).

Both xanthine oxidase and xanthine dehydrogenase are capable of using oxygen as the oxidizing substrate whereby oxyradicals are formed. However, in the case of the dehydrogenase form $NAD^+$ is the preferred substrate. In the presence of $NAD^+$ the utilization of oxygen thus will be limited (Saugstad, 1996). Pathophysiological role of xanthine dehydrogenase/oxidase. Increased conversion of xanthine dehydrogenase to its oxidase form is implicated in pathological conditions of which diseases associated with hypoxia have attracted most attention. Conversion of the enzyme is assumed to contribute to tissue damage by generation of superoxide radicals produced from oxygen during the period of re-oxygenation of tissues after re-perfusion of an area previously deprived of blood flow (McCord, 1984; Nishino, 1994). According to this hypothesis the enzyme is converted to its oxidase form in conjunction with an ischemic period. Due to the inability of ATP-regeneration in the absence of adequate oxidative phosphorylation the cellular ATP pools will also become deprived and converted to hypoxanthine during ischemia. Upon eventual tissue reoxygenation (e.g. due to recovery of blood-circulation) xanthine oxidase will however start to utilize oxygen and then oxidize hypoxanthine to xanthine, and xanthine to uric acid, thus concomitantly generating toxic oxyradicals which may cause cell damage (Nishino, 1994; Saugstad, 1996). Hypoxia induced conversion of xanthine dehydrogenase to xanthine oxygenase has been shown experimentally in hepatocytes, Kupfer cells and endothelial cells (Wiezorek et al. 1994). The xanthine dehydrogenase/xanthine oxidase enzyme can be detected in a variety of tissues such as liver, kidney, heart, central nervous system, skeletal muscle, spleen, adrenal gland, intestine, skin, kidney, lung and placenta (Wajner and Harkness, 1989; Kooij, 1994). In particular interest has been focused on the fact that the enzyme may be present in endothelial cells (Moriwaki et al., 1993) and that damage to these cells may be involved in the pathology of reperfusion injuries by capillary leakage and formation of oedema. This sort of phenomenon could be involved in, for instance, induction of increased intracranial pressure in stroke and in high altitude sickness, and be the reason of the high mortality in these conditions.

Other abnormal conditions which have been associated with xanthine oxygenase induced oxyradical formation are complications seen in preterm infants such as periventricular leucomalacia (PVL), bronchopulmonary dysplasia (BPD), and retinopathy of prematurity (ROP) (Russell et al., 1995).

It has also been shown that increased conversion of xanthine dehydrogenase to xanthine oxidase can be induced in endothelial cells in vitro by activated neutrophils (Wakabayashi et. al. 1995) and experimental evidence indicates that xanthine dehydrogenase/xanthine oxidase may be an causative enzyme under influence of a variety of inducing factors such as TNF, interferon-gamma, IL-6, IL-1, and dexamethasone (Pfeffer et al., 1994). Moreover, the promoter region of the rat xanthine dehydrogenase/xanthine oxidase gene has been isolated; its sequence suggests several possible regulatory elements, including an NF-IL6 motif upstream of the transcriptional start site (Chow et al., 1994). Moreover, pre-treatment of mice and bacterial lipopolysaccharide or interferon-alpha increases xanthine oxidase activity (see Saugstad, 1996). The results quoted here thus indicate a role of xanthine dehydrogenase/xanthine oxygenase in inflammation.

In this context the term "causative" and/or "induced" and/or "upregulated" is intended to mean that the content and/or activity of the xanthine oxidase/xanthine dehydrogenase enzyme becomes increased and/or is increased in a tissue compared to that of the normal level. A normal level is in this context intended to mean the level found in the corresponding tissue of a healthy individual.

Besides having the patophysiological roles described above it has been suggested that xanthine oxidase may be involved in a variety of other conditions such as xanthinuria, molybdenum-cofactor deficiency, gout, hyperuricemia, inflammation, airway obstruction, duodenal ulceration, arthritis, Parkinson's disease, Alzheimer's disease, paraquat intoxication, thermal skin injury, hyperthermia, pancreatitis, adult respiratory distress syndrome, nephrosis, adriamycin nephrosis, malaria, distant organ injury, cutaneous porphyrin photosensitation, inflammatory and autoimmune rheumatic diseases, rheumatoid arthritis, athereosclerosis, scleroderma and tumour promotion (see Kooji, 1994; Salim, 1994, Closa et al., 1994; Sakai et al., 1995; Misawa and Nakano, 1993; Misawa and Arai, 1993; Singh and Aggarwal, 1995; and references therein). Hepatotoxicity after viral infections (as well as after interferon treatment) was shown to be due to formation of xanthine oxidase and to oxyradical formation (see Saugstad, 1996).

Finally it should be mentioned that substantial amounts of xanthine oxidase may be released from the liver and intestine into the circulation during, e.g., hypoxia and/or shock, and that this circulating enzymatic activity may cause tissue damage at distant sites and organs of the body (Saugstad, 1996).

Known methods to prevent damage from xanthine dehydro-genase/xanthine oxidase derived free radicals. Due to the potential involvement of xanthine dehydrogenase/xanthine oxidase in the above mentioned conditions methods have been devised that are thought to interfere with xanthine dehydrogenase/xanthine oxidase or which may act on products(s) formed due to the action of these enzymes. One such method is to use an inhibitor of adenosine deaminase to limit tissue damage during reperfusion after a hypoxic episode (Xia et al., 1996). Thereby it is intended to prevent adenosine accumulated by the breakdown of cellular ATP during anoxia to form inosine which subsequently might be transformed to hypoxanthine, the very substrate for xanthine oxidase, thereby promoting the formation of superoxide radicals. Along this line the adenosine deaminase inhibitor erythro-9-(2-hydroxy-3-nonyl)adenine (EHNA) was tested experimentally in rabbits; results indicated that free radical formation was reduced and the contractile force increase in the hearts of EHNA treated animals compared to those of controls (Xia et al., 1996). One drawback with this approach is however that the adenosine deaminase inhibitor has little effect on the hypoxanthine and/or xanthine already formed during a hypoxic episode. EHNA is therefore expected to be effective only when applied prior and/or during a hypoxic period which in the clinical situation may often not be a realistic approach.

Another attempt was to use an inhibitor of xanthine oxidase to prevent breakdown of hypoxanthine/xanthine and, thereby, formation of superoxide. Xanthine oxidase inhibitors allopurinol and oxypurinol were applied experimentally by Das et al. (1987) in isolated pig hearts. The data generated by Das and co-workers did though not strongly support attenuation of the generation of free radicals by these compounds during reperfusion of the heart after a hypoxic period. In later studies it was however shown that oxypurinol reduced radical production during experimentally induced ischemia/reperfusion injury in the rat cerebral cortex (Phillis and Sen, 1993). In another attempt rats were pretreated with the xanthine oxidase inhibitor amflutizole prior to application of cerebral ischemia; this was found to strongly reduce the release of free radicals during brain reperfusion (Phillis et al., 1994). In vivo studies in experimental animals suggested that oxypurinol may afford protection against ischemic brain injury (Lin and Phillis, 1992). Recent clinical studies also suggest that allopurinol is useful in cardiac surgery when by-pass grafting is performed; it both improves postoperative recovery and reduces lipid perodixation (Coghlan et al., 1994; Castelli et al., 1995).

Free radicals have been implicated to have a role in duodenal ulceration. It was thus shown by Salim (1994) that cimetidine in combination with allopurinol, or cimetidine in combination with the radical scavenger DMSO (dimethylsulphoxide) gave remarkably better healing and reduced relapse rate in patients with refractory duodenal ulceration than did cimetidine alone.

In this context it should be stressed that there may be limitations to the use of blockers that prevent formation of uric acid from hypoxanthine and xanthine effected by administration of drugs such as EHNA, allopurinol, oxypurinol or amflutizole. This is because uric acid is one of the most important endogenous antioxidants and it may have great physiological importance by providing a tissue protective effect (see Saugstadt, 1996).

Another approach comprises the administration of a spin trap agent capable of reacting with free radicals to form a more stable species, such as N-tert-butyl-alpha-phenylnitrone (PBN) which reduced ischemic brain damage in experimental animals (Phillis and Clough-Helfman, 1990; Clough-Helfman and Phillis, 1991). The approach does not seem to have been widely applied and further evaluated. This method does not impede the formation of radicals but only traps them upon their formation, which is a clear disadvantage.

The administration of superoxide dismutase, superoxide dismutase derivatives or superoxide dismutase mimetics has also been attempted. (Closa et al., 1993; Hardy et al., 1994; Radak et al., 1995). However, superoxide dismutase may also be disadvantageous since it is known to increase ischemic re-perfusion injuries at high doses, an effect attributed to the capability of superoxide dismutase to enhance production of the highly toxic hydroxyl radical in the presence of $Fe^{2+}$ (Mao et al., 1993). Moreover, administration of a protein macromolecule such as superoxide dismutase to a human may involve many complications of pharmaceutical, pharmacokinetical, toxicological and immunological nature.

Other agents well known in the art to be useful as free radical trapping or destroying agents are DCF (2'-deoxycoformycin), catalase, vitamin E (alpha-tocopherol), vitamin C (ascorbate; ascorbic acid), glutathione, uric acid, N-acetyl-cysteine (NAC), dimethylthiourea (DMU) and betacarotens.

Hydroxyurea, hydroxyguanidine and derivatives of hydroxyguanidine. Hydroxyurea is known to possess anticarcinogenic effect (Goodman and Gilman, 1970). The mechanism of action for that effect has been suggested to be due to the inhibition of DNA synthesis by inhibition of the enzymatic conversion of ribonucleotides to deoxyribonucleotides (Goodman and Gilman, 1970). In 1972 Adamson reported that hydroxyguanidine (N-hydroxyguanidine) also possesses antitumour activity. A number of hydroxyguanidine analogs were synthesised by Bailey et al. (1973) and found to have antihypertensive effect.

A pharmaceutical preparation of the hydroxyguanidine guanoxabenz is claimed to be particularly suitable for the treatment of diarrhoea and scours (EP 0 112 061 A2). More recently several other derivatives of N-hydroxyguanidine have been synthesised, some of which were reported to exhibit antiviral and/or antineoplastic activity (Tai et al., 1984; T'ang et al., 1985; Wang et al., 1990; Doubell & Oliver,1992; Koneru et al. 1993; Hui et al., 1994). These antiviral and antineoplastic effects have been associated with a possible inhibitory effect on ribonucleotide reductase (Weckbecker et al. 1987, 1988).

The metabolism of hydroxyguanidine derivatives is essentially unknown. Hydroxyguanidine itself was reported be metabolised to guanidine when injected intraperitonally into rats (Waler & Walker 1959). The mechanism underlying this metabolism is unknown.

OBJECTS OF THE INVENTION

It is an object of the invention to provide a treatment of conditions, including preventive treatment, related to the radical generating nature of the xanthine dehydrogenase/xanthine oxidase.

It is another object of the invention to provide means and methods to prevent or reduce the formation of oxygen radicals in the human body.

It is a further object of the invention to provide means for treatment of xanthine dehydrogenase/xanthine oxidase mediated disease. A "xanthine dehydrogenase/xanthine oxidase mediated disease" is herein defined as a condition caused by the generation and/or accumulation of oxygen derived free radicals under catalysis of the xanthine dehydrogenase/xanthine oxidase enzyme. Specific examples of xanthine dehydrogenase/xanthine oxidase mediated disease are tissue damage, organ damage and inflammation caused by oxygen derived free radicals, the radicals being formed under catalysis by the xanthine dehydrogenase/xanthine oxidase enzyme. Throughout this specification the term "xanthine oxidase/xanthine dehydrogenase" has the same meaning as the term "xanthine dehydrogenase/xanthine oxidase".

It is a still further object of the intention to provide means for treatment of xanthine oxidase/anthine dehydrogenase mediated ischemic disease or condition. By "xanthine oxidase/xanthine dehydrogenase mediated ischemic disease or condition is intended a xanthine oxidase/xanthine dehydrogenase mediate disease or condition which is associated with ischemia of the body, an organ and/or tissue which is optionally followed by a period of reoxygenation.

Further objects of the invention are apparent from the following description of the invention including the appended claims.

DISCLOSURE OF THE INVENTION

Figure 1:
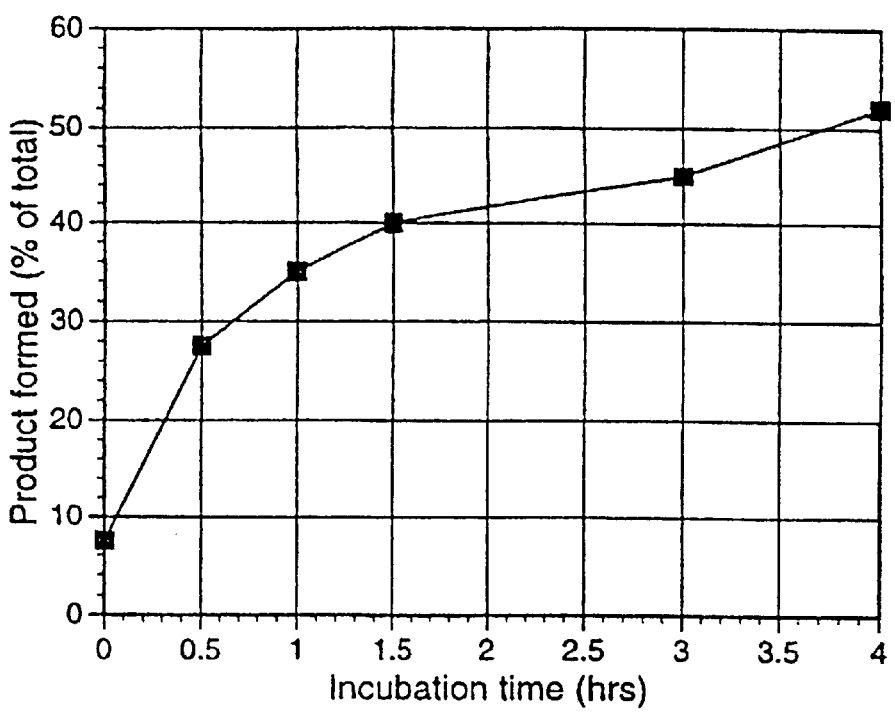
FIG. 1 shows the accumulation of guanabenz during incubation of guanoxabenz with spleen cytosol.

According to the invention is disclosed the capacity of xanthine dehydrogenase/xanthine oxidase enzyme to catalyze the reduction of hydroxyguanidines to guanidines.

Based on this finding means and methods for treatment of conditions, including preventive treatment, related to the radical generating nature of the enzymes xanthine dehydrogenase and xanthine oxidase are disclosed according to the present invention.

The present invention is based on two pairs of coupled reactions termed A,B and A,C which are explained in the following.

Reaction A is a new chemical reaction whereby a hydroxyguanidine, preferably a carbimino hydroxyguanidine, in particular an arylcarbimino hydroxyguanidine, is reduced according to the reaction scheme A:

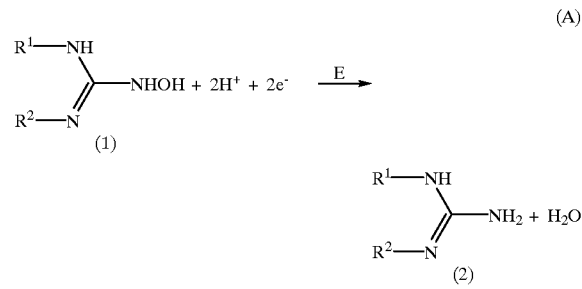

wherein E is indicates catalysis by xanthine dehydrogenase and/or xanthine oxidase. The presence of enzymatic activity in the spleen cytosol of a mammal having the capacity to promote the reaction according to reaction A is disclosed in Examples 1–3.

Reaction B is the known chemical reaction whereby hypoxanthine is oxidized to xanthine by oxygen or $NAD^+$ in the presence of xanthine oxydase and xanthine dehydrogenase, respectively.

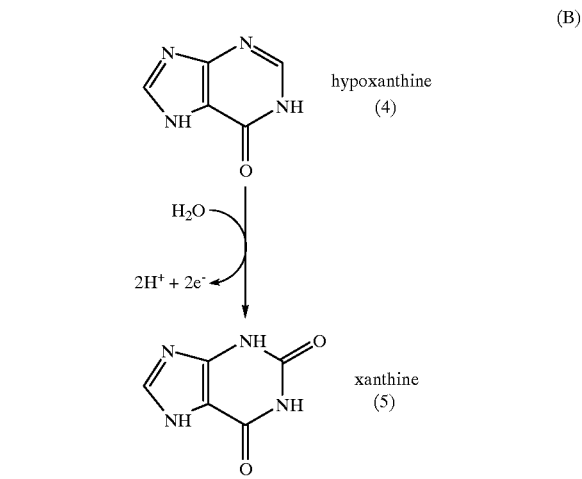

According to the invention is disclosed the capacity of a hydroxyguanidine, preferably a carbimino hydroxyguanidine and most preferably an arylcarbimino hydroxyguanidine (which term in a generic sense also comprises heteroarylcarbimino hydorxyguanidine), to substitute oxygen as oxidant in the oxidation of a purine, such as xanthine or hypoxanthine, catalyzed by the enzyme xanthine oxidase. According to this aspect of the invention the hydroxyguanidine will become reduced by accepting 2 electrons according to reaction A, while the purine concomitantly will become oxidized by the loss of 2 electrons according to reaction scheme B.

In a further, mechanistically analogous step, xanthine is oxidized to uric acid (reaction AC) with the concomitant reduction of another molecule hydroxyguanidine (reaction A).

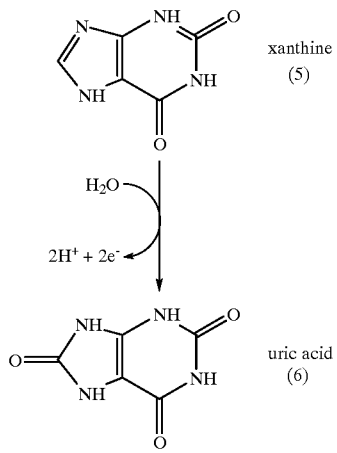

Thus is disclosed according to the invention the capacity of a hydroxyguanidine, preferably a carbimino hydroxyguanidine, particularly an arylcarbimino hydroxyguanidine, to sustain the oxidation of purines, such as xanthine and hypoxanthine, by xanthine dehydrogenase/ oxidase. Thus, in the presence of a hyroxyguanidine, purine oxidation can proceed in a tissue even in the absence of oxygen or in the presence of a limited amount of oxygen. A preferred embodiment of this aspect of the invention is given in Example 5.

A particularly important application of this aspect of the invention is the administration of the hydroxyguanidine to an animal including man, which has a generalised or localised ischemic condition. Such an ischemic condition may ensue due to inadequate blood supply of a bodyarea, such as an organ, or it could be due to inadequate content of oxygen in the blood circulating to the tissue. Thus, the administration of the hydroxyguanidine will prevent the accumulation of hypoxanthine and/or xanthine in the hypoxic area upon depletion of the ATP-pools in that area. Prevention of the accumulation of xanthine and hypoxantine is a particularly important aspect of the invention, because this avoids the eventual generation of tissue damaging oxygen derived radicals, for instance, during tissue reoxygenation. This is due to the presence of reduced levels of xanthine and/or hypoxanthine in such a condition, thereby reducing the amount of electron donors for the xanthine oxidase enzyme. Thus, administration of the hydroxyguanidine will prevent oxygen reaching the tissue from becoming reduced to noxious oxygen derived radicals by xanthine oxidase. Therefore, an important aspect of the invention is the administration of a hydroxyguanidine, preferably a carbimino hydroxyguanidine, particularly an arylcarbimino hydroxyguanidine, to a mammal including man, to prevent the accumulation of adenine nucleotides such as inosine, hypoxanthine and xanthine in tissues.

Moreover, the hydroxyguanidine will sustain the formation of uric acid according to reaction scheme C, even when such formation otherwise would not occur at all, or would proceed at a low rate due to limited supply of oxygen present in tissues, NADH, or other electron accepting compounds. A further important aspect of the invention is the concomitant formation of uric acid which has antioxidant and tissue protecting properties. Therefore, a very important aspect of the invention is the administration of a hydroxyguanidine, preferably a carbimino hydroxyguanidine, particularly an arylcarbimino hydroxyguanidine, to mammals including man, to sustain the formation of uric acid.

A particularly advantageous embodiment of the present invention aimed at sustaining the formation of uric acid in a tissue comprising the administration of a hyrdoxyguanidine to the tissue is given in Example 10.

A further important aspect of the invention is the capacity of a hydroxyguanidine, preferably a carbimino hydroxyguanidine, particularly an arylcarbimino hydroxyguanidine, to prevent and/or counteract the utilization of oxygen by the xanthine oxidase enzyme during, for instance, the oxidation of purines, such as xanthine or hypoxanthine, thereby counteracting the formation of oxygen derived radicals. A corresponding embodiment of the invention is disclosed in Example 6. Thus the administration of a hydroxyguanidine, preferably a carbimino hydroxyguanidine, particularly an alkylcarbimino hydroxyguanidine or an arylcarbimino hydroxyguanidine, to an animal including man advantageously prevents or reduces the generation of oxygen derived radicals, thereby entirely or partially suppressing tissue damage caused by such radicals and their reaction products and thus providing an important tissue protective effect.

It is furthermore understood that also other substrates than hypoxanthine and xanthine [(schemes (B) and (C)] can donate the electrons accepted by the hydroxyguanidine (scheme A). In particular endogenous substrates, such as NADH can donate electrons from xanthine dehydrogenase/ xanthine oxidase and participate in the generation of oxygen derived radicals (Harrison: In Xanthine Oxidase: Enzymology and Pathophysiology; eds. R. Harison and R. C. Bray. 66 Ist Meeting Bath Apr. 9–11, 1997. Biochem. Soc. Trans. 1997, 25, p. 786–791). Therefore, the hydroxyguanidines of the present invention are also useful for preventing the generation of free radicals also when electrons are transferred from other substrates than xanthine and hypoxanthine. Thus, the use of a hydroxyguanidine for prevention of a xanthine oxidase/xanthine dehydrogenase mediated disease or condition is not limited to the reactions (B) and (C) for the donation of electrons accepted by the hydroxyguanidine. Instead any substrate suitable for donating electron under influence of the xanthine oxidase can be used, e.g. NADH.

It is furthermore contemplated that the hydroxyguanidines of the present invention are effective in the prevention of the generation of oxygen derived radicals generated under influence by the enzymes sulphite oxidase, aldehyde oxidase and a distinct ocular oxidase (Wright and Repine: In Xanthine Oxidase: Enzymology and Pathophysiology; eds. R. Harison and R. C. Bray. 66 Ist Meeting Bath Apr. 9–11, 1997. Biochem. Soc. Trans. 1997, 25, p. 799–804). This is because of the structural similarities of these enzymes with xanthine dehydrogenase/xanthine oxidase, all these enzymes having homologous primary structure and similar organisation which include ironsulphur centres, being flavoproteins and having molybdenum sites. It is thus contemplated that hydroxyguanidines will interact in a similar manner on the sulphite oxidase, aldehyde oxidase and the distinct ocular oxidase as with the xanthine dehydrogenase/xanthine oxidase enzymes by accepting electrons and thereby preventing molecular oxygen from taking said electrons and thus preventing generation of superoxide and other oxygen derived free radicals. Included in the present invention is therefore also the use of the hydroxyguanidines of the invention for the prevention of the generation of oxygen derived radicals by sulphite oxidase, aldehyde oxidase and the ocular oxidase. In the present patent included into the term "xanthine oxidase/xanthine dehydrogenase mediated ischemic disease or condition" is also the disease or condition caused by generation of oxygen derived radicals under influence of sulphite oxidase, aldehyde oxidase and ocular oxidase.

Specific embodiments of these aspects of the invention comprise administration of a hydroxyguanidine, preferably a carbimino hydroxyguanidine, particularly an arylcarbimino hydroxyguanidine, to a tissue to for tissue protection, thereby eventually affording a reduction of the size and severity of tissue damage, as well as improved recovery and healing if such damage has occurred. Important examples of this aspect of the invention comprise the administration of a hydroxyguanidine, preferably a carbimino hydroxyguanidine, particularly an arylcarbimino hydroxyguanidine, to a person in which generalized or local hypoxic condition prevails and which condition is optionally followed by a period of increased supply of oxygen e.g. in the course of therapeutic tissue reoxygenation. Examples of such conditions are heart infarction, angina pectoris cerebrovascular infarction, arrythmias of the heart, circulatory shock, transient ischemic attacks of the CNS, arterial occlusion, arterial tromboembolism, bowel torsion with strangulation, testicular torsion, lung embolus, cardiac surgery including by pass grafting, localised organ surgery involving reduced blood flow e.g. due to lowering of blood pressure, partial or total occlusion of arterial blood flow, or high altitude sickness. Moreover, susceptible to treatment comprising the administration of a hydroxyguanidine, preferably a carbimino hydroxyguanidine, particularly an arylcarbimino hydroxyguanidine, are preterm children whose survival rate and long abilities in later life will improve. In particular this is seen in the preterm children treated with oxygen. Hydroxyguanidine administration will, in particular, prevent of the development of periventricular leucomalacia (PVL), broncho-pulmonary dysplasia (BPD), and retinopathy of prematurity (ROP).

Another important aspect of the invention comprises prophylactive administration of hydroxyguanidine, preferably a carbimino hydroxyguanidine, particularly an arylcarbimino hydroxyguanidine, that is, prior to the occurrence of hypoxic conditions to afford protection and avoid tissue damage. Particular important examples of this aspect of the invention is such administration to a person suffering from angina pectoris and/or is in risk of having an heart infarction and/or reinfarction of the heart.

Another specific example where reperfusion injuries take place is rheumatoid arthritis (see (Blake et al.: In Xanthine Oxidase: Enzymology and Pathophysiology; eds. R. Harison and R. C. Bray. 66 Ist Meeting Bath Apr. 9–11, 1997. Biochem. Soc. Trans. 1997, 25, p. 812–816). Thus, during increased inflammation of the joint pressure may exceed the capillary perfusion pressure which may lead to occlusion of the blood flow in the synovial capillary bed. However, during rest the pressure of the joint may become reduced allowing reperfusion to occur. This will result in immediate generation of oxygen derived radicals via the xanthine oxidase pathway. Thus, in rheumatoid arthritis the joint is subjected to a repeated reperfusion injury syndrome which may be (at least partly) responsible for the sustained inflammation and bone erosions seen in the disease. Therefore, administration of the hydroxyguanidines of the present invention will be useful in the treatment of rheumatoid arthritis. Moreover, accordingly, rheumatoid arthritis is part of a xanthine oxidase/xanthine dehydrogenase mediated ischemic disease.

Still another specific example of a disease where reperfusion injuries take place is glaucoma. Glaucoma arises due to increased ocular pressure which results in perturbation or complete stop of retinal blood flow. If ocular pressure is eventually reduced reperfusion injury of the retina may ensue due to xanthine oxidase mediate production of oxygen derived radicals leading to delayed injury of the retina (see Roth et al. Current Eye Res. 1997, 16, 875 885). Therefore also in glaucoma the administration of the hydroxyguanidine of the present invention will have a positive treatment effect. Accordingly glaucoma is also part of a xanthine oxidase/xanthine dehydrogenase mediated ischemic disease.

A further particularly advantageous embodiment of the present invention aimed for the treatment of reperfusion injury in the heart is given in Example 9.

Another variation of this aspect of the invention comprises administration of a hydroxyguanidine, preferably a carbimino hydroxyguanidine, particularly an arylcarbimino hydroxyguanidine, to a person being at a high altitude or any other locality having an oxygen pressure substantially reduced in respect to that prevailing at sea level. Such administration is useful for counteracting the dangerous effects of a low ambient oxygen pressure, such as the formation of lung oedema and/or brain oedema. This is a desired protective effect of a hydroxyguanidine, preferably a carbimino hydroxyguanidine, particularly an arylcarbimino hydroxyguanidine, which may be enhanced by continuing administration for some time after that the person exposed to such reduced oxygen pressure has returned to an environment with normal (low altitude or sea level) oxygen pressure.

According to another aspect of the invention a hydroxyguanidine, preferably a carbimino hydroxyguanidine, particularly an arylcarbimino hydroxyguanidine, is administered to an organ removed from an animal, which preferably is a mammal including a human, intended for transplantation to another animal of the same or another species, including a human, the purpose being to protect the organ from tissue damage by oxygen radicals, in particular since such damage may occur when the organ is reoxygenized upon establishment of circulatory contact with the blood of the new host.

Still another aspect of the invention concerns the administration of a hydroxyguanidine, preferably a carbimino hydroxyguanidine, particularly an arylcarbimino hydroxyguanidine, to a person suffering from a condition associated with the generation of oxygen derived radicals. In particular such administration will pertain to conditions associated with the generation of oxyradicals by the xanthine oxidase/xanthine dehydrogenase enzyme. Such an increased (upregulated) generation of oxyradicals can be seen in disease associated with an increased (upregulated) activity of xanthine oxidase. Diseases of this kind include inflammatory conditions of unidentified origin, airway obstruction, asthma, duodenal ulceration, ulcerous colitis, Crohn's disease, arthritis, Parkinson's disease, paraquat intoxication, thermal skin injury, hyperthermia, pancreatitis, adult respiratory distress syndrome, nephrosis, adriamycin nephrosis, renal damage associated with the administration of parenteral X-ray contrast media, malaria, distant organ injury, cutaneous porphyrin photosensitation, inflammatory and autoimmune rheumatic diseases, rheumatoid arthritis, atherosclerosis, scleroderma, hepatitis, hepatic damage caused by viral infection, increased intracranial pressure, spinal cord injury, bacterial meningitis, hepatic damage caused by treatment with interferon or hepatic damage caused by treatment with any other drug or xenobiotic, as well as in any condition showing upregulated expression of the xanthine dehydrogenase/xanthine oxidase enzyme. A preferred variation of this aspect of the invention comprises such administration to a person suffering from a condition characterized by the presence of increased amounts (in relation to those in a healthy animal or person) of xanthine oxidase in the blood, in particular persons releasing the xanthine oxidase from liver and/or intestine during hypoxia and/or shock.

In order to provide enhanced or additive effects the hydroxyguanidines of the present invention may also be administered in combination with other drug(s) capable of reducing or preventing effects caused by free radicals. Examples of such combinations are the administration of a hydroxyguanidine in combination with an adenosine deaminase inhibitor, such as EHNA. Other examples comprise administering hydroxyguanidines in combination with free radical scavengers, such as DMSO, and/or in combination with spin trap agents, such as PBN, and/or in combination with superoxide dismutase, superoxide dismutase derivatives or superoxide dismutase mimetics.

Other agents that can be advantageously administered in combination with the hydroxyguanidines of the present invention in order to provide enhanced or additative effect are DCF (2'-deoxycoformycin), catalase, vitamin E (alpha-tocopherol), vitamin C (ascorbate; ascorbic acid), glutathione, uric acid, N-acetyl-cysteine (NAC), dimethylthiourea (DMU) or beta-carotens.

According to still another aspect of the invention there are disclosed hydroxyguanidines the reduction of which is catalyzed by xanthine dehydrogenase/xanthine oxidase, and which are useful in the present invention.

By xanthine oxidase/xanthine dehydrogenase mediated ischemic disease or ischemic condition is intended a xanthine oxidase/xanthine dehydrogenase mediated disease which is associated with ischemia of the body, an organ and/or tissue optionally followed by reoxygenation.

In addition it is conceivable that the reduction product [compound (2) according to scheme (A)] of a hydroxyguanidine of the present invention may provide an enhanced or additive effect to the effect caused by the hydroxyguanidine itself. The administration of the reduction product of a hydroxyguanidine [compound (2) according to scheme (A)], in the presence of a hydroxyguanidine of the present invention, is therefore also part of the present invention.

The compounds of the present invention may be used in the form of pharmaceutically-acceptable acid addition salts derived from inorganic or organic acids. These salts include, but are not limited to, the following: acetate, adipate, alginate, aspartate, benzoate, benzenesulfonate, sulfate, bisulfate, butyrate, camphorate, camphorsulfonate, citrate, cyclopentanepropionate, digluconate, dodecylsulfate, ethanesulfonate, fumarate, gluco-heptonate, glycerophosphate, hemisulfate, heptanoate, hexanoate, hydrochloride, hydro-bromide, hydroiodide, 2-hydroxy-ethanesulfonate, lactate, maleate, methanesulfonate, nicotinate, 2-naphthalenesulfonate, oxalate, palmote, pectinate, persulfate, 3-phenyl-propionate, phosphate, picrate, pivalate, propionate, succinate, tartrate, thiocyanate, tosylate, and undecanoate. These salts can be prepared in situ during the final isolation and purification of the compounds, or by separately reacting the free base with a suitable organic or inorganic acid.

Furthermore the compounds of the invention may be used in the form of prodrugs, such as ester prodrugs, from which the respective free compoundis released in the body upon administration. Such prodrugs include, for instance, esters of the compounds of the invention, such as acetate, benzoate, pivaloate, etc.

Another form of administration as prodrug is the administration of the reduction product [compound (2) according to scheme (A)] of a hydroxyguanidine, in the case that metabolic activation leads to formation of a hydroxyguanidine, carbiminohydroxyguandine or arylcarbiminohydroxyguanidine.

The compounds of the invention will be administered in therapeutically effective amounts. By a "therapeutically-effective amount" is meant a sufficient amount of the compound to treat or prevent disorders. The specific therapeutically-effective dose level for any particular patient will depend upon a variety of factors including the disorder being treated and the severity of the disorder or the protective effect sought; activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed.

The total daily dose of a compound according to the invention administered in single or divided doses to person may be for example, from about 0.1 to about 100 mg/kg body weight, or more usually, from about 0.2 to about 50 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose. However, in severe cases and/or for acute treatment higher doses, such as up to 10,000 mg of one or several compounds of the invention may be administered in a single dose which may be given in multiple consecutively administered portions. The amount of active ingredient that may be combined with the carrier materials to produce a single dosage form will vary depending upon the host treated, the particular treatment and the particular mode of administration.

The compounds of the present may be administered orally, parenterally, by inhalation spray, rectally, or topically in dosage unit formulations containing conventional non-toxic pharmaceutically-acceptable carriers, adjuvants, and vehicles as desired. The term parenteral as used herein includes subcutaneous injections, intravenous, intramuscular, intrastemal injection, or infusion techniques. Liquid dosage forms for oral administration may include pharmaceutically-acceptable emulsions, microemulsions, solutions and suspensions containing inert diluents such as water. Such compositions may also comprise adjuvants, such as wetting agents; emulsifying and suspending agents; and sweetening, flavouring and perfuming agents, Injectable preparations, for example, sterile injectable aqueous or oleaginous suspensions may be formulated according to the known art using suitable dispersing or wetting agents and suspending agents. The sterile injectable preparation may also be sterile injectable solution or suspension in a nontoxic parenterally acceptable diluent or solvent, for example, as solution in 1,3-butanediol. Among the acceptable vehicles and solvents that may be employed are water, Ringer's solution, isotonic sodium chloride solution. In addition, sterile fixed oils are conventionally employed as a solvent or suspending medium. Fixed oils and fatty acids, such as oleic acid may be employed in the preparation of injectables.

The injectable formulation can be sterilized, for example, by filtration through a bacteria- or virus-retaining filter, by radiation, or by incorporation sterilizing agents in the form of sterile solid compositions which can be dissolved or dispersed in sterile water or other sterile injectable medium just prior to use. There are various methods for delaying absorption of a drug known in the art such as, for instance, to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with suitable suitable nonirritating excipients known in the art and having a melting point appropriate for such administration, that is of about 30°. Solid dosage forms for oral administration may include capsules, tablets, pills, and granules. In such solid dosage forms, the active compound may be admixed with at least one inert diluent such as sucrose, lactose, or starch. Such Dosage forms may also comprise additional substances other than inert diluents, e.g., lubricating agents such as magnesium stearate. In the case of capsules, tablets, and ills, the dosage forms may also comprise buffering agents. Tablets and pills can additionally be prepared with enteric coatings, for instance coatings which release the drug in the small intestine but not in the stomach. In regard of the preparation of tablets for oral administration particular reference is made to Pharmaceutical Dosage Forms, Vol. 1–3, Lieberman A et al., Eds., 2nd Ed. Marcel Dekker, New York 1989–90.

The compounds of the invention may also be administered topically, transdermally or by inhalation in form of ointments, pastes, creams, lotions, gels, powders, solutions, sprays, patches or inhalants. The compound is admixed under sterile conditions with a pharmaceutically-acceptable carrier and any preservatives or buffers that may be required. Ophthalmic formulations are also contemplated as being within the scope of this invention.

The present agents can also be administered in the form of liposomes. As is known in the art, liposomes are generally derived from phospholipids or other lipid substances. Liposomes are formed by mono- or multi-lamellar hydrated so liquid crystals that are dispersed in an aqueous medium. Any non-toxic physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lechithins), both natural and synthetic. Methods to form liposomes are known in the art. See, for example, Prescott, Ed., Methods in Cell Biology, Vol. .XIV, Academic Press, New York, N.Y. 1976, pp. 33 et seq.

The compounds of this invention can be administered alone or in combination with other agents.

Since the capacity of being an oxidisable substrate for xanthine dehydrogenase/xanthine oxidase is one shared by a large majority of hydroxy guanindines this entire class of compounds is considered useful in the invention.

According to the invention are disclosed particular hydroxyguanidines which are useful in the prevention and treatment of conditions related to the formation of oxygen radicals by the action of xanthine dehydrogenase/xanthine oxidase.

Preferred is a carbimino hydroxyguanidine of the formula (7)

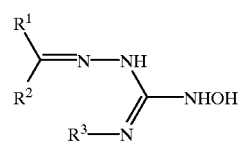

(7)

in which $R^1$, $R^2$ and $R^3$ of (7) are selected independently of each other from the group consisting of H, alkyl, alkenyl, cykloalkyl, cykloheteroalkyl, cykloalkenyl, cykloheteroalkenyl, alkynyl, aryl, heteroaryl and/or a bridge of from 4 to 5 carbon or heteroatoms connecting $R^1$ and $R^2$ of (7) or of from 0 to 1 carbon or heteroatom(s) connecting $R^2$ and $R^3$ of (7), thus in case of bridge creating 5- or 6-membered cycle which may optionally be fused with cycloalkyl, cykloheteroalkyl, cykloalkenyl, cykloheteroalkenyl, aryl or heteroaryl, and one or more hydrogen(s) in $R^1$, $R^2$ and/or $R^3$ of (7) optionally being exchanged for alkyl, alkyenyl, cykloalkyl, cykloheteroalkyl, cykloalkenyl, cykloheteroalkenyl, alkynyl, aryl, heteroaryl, halogen, functional group and/or alkyl, alkenyl, cykloalkyl, cykloheteroalkyl, cykloalkenyl, cykloheteroalkenyl, alkynyl, aryl, heteroaryl or functional group in which one or more hydrogen(s) are exchanged for halogen or functional group.

Particularly preferred is an arylcarbimino hydroxyguanidine wherein $R^1$ in (7) is aryl or heteroaryl substituted by one or several of functional group, halogen, alkyl, alkyenyl, alkynyl, cycloalkyl, cycloheteroalkyl, cycloalkenyl, cycloheteroalkyenyl.

Even more preferred is a compound according to the formula

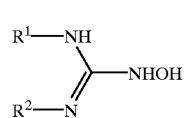

(1)

wherein $R^1$ is —N=$CR^3R^4$;
wherein $R^2$ is selected from the group consisting of H, alkyl, alkenyl, cycloalkyl, cycloalkenyl, cycloheteroalkyl, cycloheteroalkenyl, alkynyl, aryl, heteroaryl, a single bond of $R^3$, and a carbon or a heteroatom connected to $R^3$;
wherein $R^3$ and $R^4$ are selected independently of each other from the group consisting of H, alkyl, alkenyl, cycloalkyl, cycloalkenyl, cycloheteroalkyl, cycloheteroalkenyl, alkynyl, aryl, heteroaryl, and a bridge of from 4 to 5 carbon or heteroatoms forming a 5- or 6-membered ring, which optionally is fused with cycloalkyl, cycloheteroalkyl, cycloalkenyl, cycloheteroalkenyl, aryl or heteroaryl;
and wherein $R^3$, in addition is selected from a single bond of $R^2$, and a carbon or a heteroatom connected to $R^2$ such as to form a 5- or 6-membered ring which optionally is fused with cycloalkyl, cycloheteroalkyl, cycloalkenyl, cycloheteroalkenyl, aryl or heteroaryl;
and wherein optionally one or several hydrogen(s) in $R^2$, $R^3$, $R^4$ are independently exchanged for alkyl, alkenyl, cycloalkyl, cycloheteroalkyl, cycloalkenyl, cycloheteroalkenyl, alkynyl, aryl, heteroaryl, halogen or functional group, and one or more hydrogen(s) in said alkyl, alkenyl, cycloalkyl, cycloheteroalkyl, cycloalkenyl cycloheteroalkenyl, alkynyl, aryl, heteroaryl, functional group being independently exchanged for halogen or functional group.

However, most preferred is a carbimino hydroxyguanidine of the formula (1)

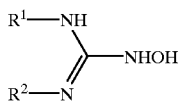

(1)

in which $R^1$ is —N=$CR^3R^4$ wherein $R^2$, $R^3$, $R^4$ are selected independently of each other from the group consisting of H, alkyl, alkenyl, cycloalkyl, cycloalkenyl, alkynyl, aryl, heteroaryl, in which one or two carbon atoms may be exchanged for heteroatom and any hydrogen may be exchanged for fluorine and/or a functional group and/or a bridge of from 0 to 5 carbon atoms connecting $R^2$ and $R^3$ or $R^3$ and $R^4$ so as to create a 5- or 6-membered ring which may be fused with cycloalkyl, cycloheteroalkyl, cycloalkenyl, aryl or heteroaryl and which may contain 1 or 2 double bonds and in which one or two carbon atoms may be exchanged for one or two, respectively, of heteroatom.

Particularly preferred is an arylcarbimino hydroxyguanidine wherein $R^3$ of (1) is aryl or heteroaryl substituted by one or several of functional group, alkyl, alkenyl, cycloalkyl, cycloalkenyl, alkynyl.

The term "alkyl" as employed herein by itself or as part of another group includes a straight or branched hydrocarbon chain of up to 18, preferably from 1 or 8 carbon atoms, such as methyl, ethyl, propyl, iso-propyl, tert-butyl, butyl, pentyl, hexyl, heptyl, octyl.

The term "alkenyl" as employed herein by itself or as part of another group includes a straight or branched hydrocarbon chain of up to 18, preferably from 2 to 8 carbon atoms comprising one or several carbon-carbon double bonds, such as propenyl, butenyl, pentenyl.

The term "cycloalkyl" as employed herein by itself or as part of another group refers to cyclic hydrocarbons containing from 3 to 12 carbons, preferably 3 to 8 carbons, such as cyclopropyl, cyclobutyl, cyclopentyl, cyclohexyl, cycloheptyl, cyclooctyl, and may be fused with 1 or 2 cycles which are independently selected from each other from the group consisting of cycloalkyl, cycloheteroalkyl, cycloalkenyl, cycloheteroalkenyl, aryl and heteroaryl.

The term "cycloheteroalkyl" as employed herein by itself of as part of another group refers to cycloalkyl where one or several carbon atoms are exchanged for heteroatom.

The term "cycloalkenyl" as employed herein by itself or as part of another group refers to cycloalkyl containing one or several carbon-carbon double bonds, such as cyclopentenyl and cyclohexenyl.

The term "cycloheteroalkenyl" as employed herein by itself or as part of another group refers to cycloheteroalkyl where one or more bonds between carbons, carbon and heteroatom, or heteroatoms are double.

The term "alkynyl" as employed herein by itself or as part of another group refers to alkyl containing one or several carbon-carbon triple bonds.

The term "aryl" as employed herein by itself or as part of another group refers to phenyl in which one or more hydrogens may be optionally substituted by halogen or alkyloxy, and which may optionally be fused with 1 or 2 cycles which are independently selected of each other from the group consisting of cycloalkyl, cycloheteralkyl, cycloalkenyl, cycloheteroalkenyl, aryl and heteroaryl.

The term "aryl" as employed herein by itself or as part of another group also refers to phenyl in which one or more hydrogens may be substituted by alkyl, fluorinated alkyl, alkenyl, fluorinated alkenyl, cykloalkyl, fluorinated cykloalkyl, cycloheteroalkyl, cycloalkenyl, cycloheteroalkenyl, alkynyl, aryl, heteroaryl and/or functional group, and which may be optionally fused with 1 or 2cycles which are independently selected from each other from the group consisting of cycloalkyl, cycloheteroalkyl, cycloalkenyl, cycloheteroalkenyl, aryl and/or heteroaryl.

The term "heteroaryl" as employed herein by itself or as part of another group refers to a 5- to 12-membered aromatic ring, preferably 5- to 6-membered aromatic ring, which includes one or more heteroatoms, which may be optionally fused with 1 or 2 cycles which are independently selected from each other from the group consisting of cycloalkyl, cycloheteroalkyl, cycloalkenyl, cycloheteroalkenyl, aryl and heteroaryl.

The term "heteroaryl" as employed herein by itself or as part of another group also refers to a 5- to 12-membered aromatic ring, preferably 5- or 6-membered aromatic ring, which includes one or more heteroatoms, and in which one or more hydrogens may be substituted by alkyl, fluorinated alkyl, alkenyl, fluorinated alkenyl, cykloalkyl, fluorinated cykloalkyl, cycloheteroalkyl, cycloalkenyl, cycloheteroalkenyl, alkynyl, aryl, heteroaryl and/or functional group, and which may be optionally fused with 1 or 2 cycles which are independently selected from each other the group consisting of cycloalkyl, cycloheteroalkyl, cycloalkenyl, cycloheteroalkenyl, aryl and/or heteroaryl.

The term "halogen" as employed herein by itself or as part of another group refers to chlorine, bromine, fluorine and iodine with chlorine being preferred.

The term "heteroatom" as employed herein by itself or as part of another group refers to nitrogen, oxygen or sulphur, to which one or more hydrogens may be connected according to valence and in the case of nitrogen one oxygen may be optionally connected to it by donor-acceptor bond, thus forming N-oxide.

The term "functional group" as employed herein by itself or as part of another group refers to amino, alkylamino, dialkylamino, aryloxy, arylamino, heteroarylamino, hydroxy, alkylhydroxy, fluorinated alkylhydroxy, cyano, carboxy, alkylcarboxy, carboxyalkyl, arylcarboxy, carboxyaryl, halogen, nitro, hydroxyamino, acyl, fluorinated acyl, nitroso, sulfonyl, sulfinyl, thio, alkylthio, arylthio, aminoguanidino, aminohydroxyguanidino, iminoguanidino, imino-hydroxyguanidino, guanidino, hydroxyguanidino, guanidinoamino, hydroxyguanidinoamino, hydroxyguanidinoimino or guanidinoimino.

The term "fused" as employed herein by itself or as part of another group refers to two or three cycles having one or more common atoms, the preferred maximum number of fused cycles being three.

The term "fluorinated" as employed herein by itself or as part of another group refers to that in following term one or several hydrogens are substituted with fluorine.

Most preferred compounds of the invention are selected from arylcarbimino hydroxyguanidines or heteroarylcarbimino hydroxyguanidines in which hydrogens of the aryl group is substituted by one or several of: alkyl, aryloxy (in which substituent one or several hydrogen may be substituted by fluorine), halogen, hydroxy.

Particularly preferred are also guanoxabenz and the compounds DWO1, DWO2, DWO3 DWO4, DWO5, DWO6, DWO7, DWO8, LW01, LW04, LT5, LT7, LT10, LT11, PR1, PR2, PR4, PR5, PR6, PR8, PR10, PR11, PR12, PR13, PR14, PR15, PR16, PR17, PR18, PR19, PR20, PR21, EN10, EN12, EN18, EN16, EN20. Hydroxyguanidines such as guanoxabenz, which is particularly preferred, are known in the art. However, most preferred is PR5 due to its high activity as is disclosed in Example 7.

The present invention also relates to a compound which is a pro-drug of the aforementioned compounds of the invention, and which in mammals including man, is converted to a molecule which is a hydroxyguanidine, preferably a carbimino hydroxyguanidine, most preferred, an arylcarbimino hydroxyguanidine.

A particular important pro-drug is the compound according to formula (2) which, according to reaction scheme (D), is capable of forming the compound (1) of the present invention.

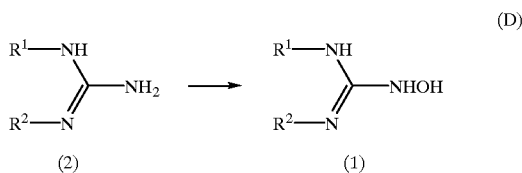

Moreover, as the hydroxyguanidine (1) of the present invention according to the reaction scheme (A) will form compound (2) reaction scheme (D) serves as a mode for regeneration of the hydroxyguanidine of the present invention. The metabolic conversion of guanabenz to guanoxabenz by liver cytochrome P450 enzymes have recently been described (Clement and Demesmeaker, Drug. Metab. Dispos., 1997, 25, 1266–1271). A large capacity of a compound according to formula (2) to form the hydroxyguandine, carbaminohydroxyguanidine or arylcarbiminohydroxyguanidine of the present invention is thus particularly advantageous property of a hydroxugunaidine of the present invention, as this will continuously in the body regenerate the hydroxyguanidine consumed according to reaction scheme (A). This aspect of the invention is advantageous irrespectively if the hydroxyguanidine of the invention is administered as pro-drug complying to formula (2) or as the hydroxyguanidine itself complying to formula (1).

According to the invention is also disclosed a method of assaying the hydroxyguanidine reducing activity. A preferred embodiment (Example 2) of this method takes advantage of particular properties of the known hydroxyguanidine guanoxabenz:

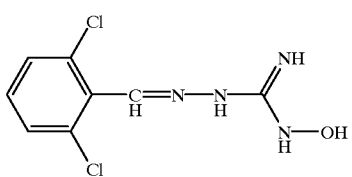

Thus, upon reduction of guanoxabenz according to reaction A a product called guanabenz is formed which can easily be measured by virtue of its high binding affinity for α2-adrenergic receptors.

As is further shown in Example 3 it can be demonstrated according to the invention that the enzymatic activity present in spleen cytosol can be purified to essential homogeneity and be shown to be identical with the xanthine dehydrogenase/xanthine oxidase enzyme.

As has been explained earlier the oxidation of purines, such as hypoxanthine and xanthine, by xanthine oxidase takes place in the presence of oxygen under formation of superoxide radical ($.O_2$-) and, to a lesser extent, hydrogen peroxide ($H_2O_2$). In the following such oxygen-based radicals, which include the superoxide radical, the perhydroxyl radical and the hydroxyl radical, will be collectively referred to as oxygen derived radicals. Moreover, as an alternative term oxyradical is used which, mutatis mutandis, is intended to have the identical meaning as oxygen derived radical. Hydrogen peroxide is a prominent source of such radicals. In Example 4 the enzymatic reduction of hydroxyguanidines is demonstrated to be catalyzed by xanthine oxidase isolated from bovine milk in the presence of xanthine. In the absence of xanthine no reduction is seen.

According to another aspect of the invention are disclosed methods for selection of a hydroxyguanidine, preferably a carbimino hydroxyguanidine, most preferred an arylcarbimino hydroxyguanidine, for use in the invention. In the testing of a hydroxyguanidine for its capacity to undergo reaction A coupled to reaction B and/or reaction C use is made of the measurement of one or several of the following parameters:

- the apparent affinity of the hydroxyguanidine for the xanathine oxidase enzyme;
- the $K_m$ for the reduction of the hydroxyguanidine by the xanthine oxidase enzyme,
- the maximal velocity ($V_{max}$) for the reduction of the hydroxyguanidine by the xanthine oxidase enzyme; and
- the maximal oxidation rate of xanthine and/or hypoxanthine by the xanthine oxidase enzyme afforded by the hydroxyguanidine.

In some embodiments of this aspect of the invention the above mentioned capacities are measured in the presence of oxygen whereas in other embodiments they are measured in its absence.

In a yet further embodiment of this aspect of the invention the capacity of the hydroxyguanidine to reduce the formation of oxygen derived radicals is measured. In Example 7 is shown an exemplary assay for the capacity of a series of hydroxyguanidines to sustain the oxidation of xanthine by the xanthine oxidase enzyme in the absence of oxygen. In Example 6 is shown an exemplary assay for measuring the capacity of a hydroxyguanidine to prevent the formation of oxyradicals.

In further embodiments of the invention a pronounced tendency of the hydroxyguanidine to undergo reaction A is an undesired property of the hydroxyguanidine. "Pronounced tendency" as employed herein refers to a tendency which is in the range that possessed by the hydroxyguanidines disclosed in Example 7. The fact that a pronounced tendency is an undesired property for certain applications is due to the increased breakdown rate of the hydroxyguanidine resulting in a short half life of the hydroxyguanidine when administered to a mammal including man. Moreover a pronounced tendency to undergo the reaction according to scheme A may result in a low local concentration of the hydroxyguanidine in a tissue where its effect is most desired. An increased half life of a coupound according to the invention, therefore, may be an advantage under certain circumstances. Compounds according to the invention displaying a moderate tendency for reduction in reaction A can be identified by using the above selection criteria. Exemplary hydroxyguanidines showing a moderate capacity as described herein is DWO3 the structure and properties of which are disclosed in Example 7.

According to the invention is also disclosed the concomitant administration of a xanthine dehydrogenase/xanthine oxidase blocking drug with a hydroxyguanidine, in particular a carbi-mino hydroxyguanidines, most preferred an arylcarbimino hydroxyguanidine, the breakdown of which is desired to be inhibited. Such xanthine dehydrogenase/xanthine oxidase blocking drug may preferably be selected from the group of allopurinol, oxypurinol and amflutizole.

Throughout this patent

"paraquat" refers to 1,1'-dimethyl-4,4'-bipyridinium,
"adriamycin" to (8S-cis)-10-[(3-amino-2,3,6-trideoxy-α-L-lyxo-hexopyranosyl)oxy]-7,8,9,10-tetrahydro-6,8,11-trihydroxy-8-(hydroxyacetyl)-1-methoxy-5,12-naphthacenedione,
"allopurinol" to 1H-pyrazolo[3,4-d]pyrimidin-4ol,
"oxypurinol" to 1H-pyrazolo[3,4-d]pyrimidin-4,6-diol and
"amflutizole" to 4-amino-3-[3-(trifluoromethyl)-phenyl)]-5-isothiazolecarboxylic acid.

The following examples are intended for the detailed illustration of various embodiments of the invention but should be in no way considered as limitations of it.

EXAMPLE 1

Identification of a hydroxyguanidine reducing activity in the spleen

Preparation of crude spleen cytosol. Rat spleens were homogenised (1:10 w/v) in ice-cold 20 $\mu$M Tris, 1.5 mM EDTA, pH 7.5 with glass/Teflon homogenizer. The homogenate was centrifuged at 30,000×g for 15 min at 4° C. and stored frozen at −80° C. After thawing the supernatant was centrifuged at 70,000×g for 1 hr at 4° C. and used for the assays.

Identification of a reaction product derived from hydroxyguanidine. Crude spleen cytosol was incubated at 25° C. with 70 $\mu$M guanoxabenz (2(2,6-dichlorophenyl)methylene-N-hydroxyhydrazine carboxi-imidamide) in the presence of 25 mM Tris-HCl, 0.75 mM EDTA, the total volume being 4 ml. Aliquots of 250 $\mu$l were then withdrawn from the reaction mixture after 1, 30, 60, 90 or 240 minutes and heated in a water bath to 80° C. for 5 minutes. The sample was then centrifuged and the supernatant filtered through a 0.22 $\mu$m Millipore filter whereafter 200 $\mu$l of the filtrate was injected into a reverse phase chromatography column (Waters Symmetry C8) equilibrated in 40% methanol, 60% 10 mM Na-acetate buffer, pH 4.5. The elution speed was 0.5 ml/min and the eluted substances were detected by a UV-monitor set at 260 nm. In separate experiments it was shown that for this chromatographic set-up guanoxabenz and guanabenz become distinctly separated; the retention time for guanoxabenz being about 11.5 min, and that for guanabenz about 13 min The results of this experiment showed that with increasing incubation times the peak corresponding to guanabenz became progressively larger while the peak corresponding to guanoxabenz became correspondingly smaller. Thus, after 1 minute incubation only 5% of the UV-absorption corresponded to the guanabenz peak whereas 95% occurred in the guanoxabenz peak. After 1 hour the guanabenz peak represented about ⅓ and the guanoxabenz peak ⅔ of total the absorbance of the chromatograms. After 4 hours both peaks were of about equal size. Chromatograms never showed any significant other peaks than those corresponding to guanoxabenz or guanabenz. In FIG. 1 is shown exemplary details on the time course of appearence of the product. In FIG. 1 the ordinate shows the percent of the area under the HPLC peak for the guanabenz peak of the sum of the areas under the HPLC peaks for the guanabenz and the guanoxabenz peaks.

Preparation of the enzymatic reaction product for NMR-analysis. To obtain enough of the product for NMR studies guanoxabenz (500 $\mu$M) was pre-incubated with the crude spleen cytosol for 1 hr. In these incubations the medium was supplemental with $MgCl_2$ (2 mM) and DTT (2 mM) because the additions were found to enhance the enzymatic activity. Total volume of the reaction mixture was 4 ml. After the incubation the reaction mixture was boiled, centrifuged and filtered, essentially as described above, and aliquots of the materials injected onto the HPLC column. The results showed that a peak corresponding to guanabenz represented more than 99% of the UV-absorbing material (260 nm) eluted from the column. The fractions containing the product peak were collected, pooled and lyophilized and then subjected to NMR-analysis.

Characterization of the reaction product by NMR. NMR spectra were recorded at 270.2 MHz in $CDCl_3$ using JEOL JNM270 spectrometer equipped with a standard 5 mm probe and, for the micro sample observation, a 5 mm probe with inverse configuration. Data were processed using the DELTA processing package. Reference spectra for guanabenz and guanoxabenz were recorded in DMF-d7 at concentration 0.095 and 0.090 molar respectively. Sample volumes were 0.6 ml, and a standard 5 mm probe was used. The product (approximately 80 $\mu$g) produced by the enzymatic reduction of guanoxabenz was dissolved in two drops of the same deuterated solvent, giving a concentration of approximately 0.01 molar. This solution was drawn into a capillary tube with internal diameter 1 mm, which was then sealed with modelling clay (care was taken to ensure that the solution did not come into contact with the modelling clay, so that the sample was kept free of contaminants). The capillary tube was suspended coaxially in a standard 5 mm NMR tube and the spectra obtained using a probe configured for inverse detection.

Figure 2:
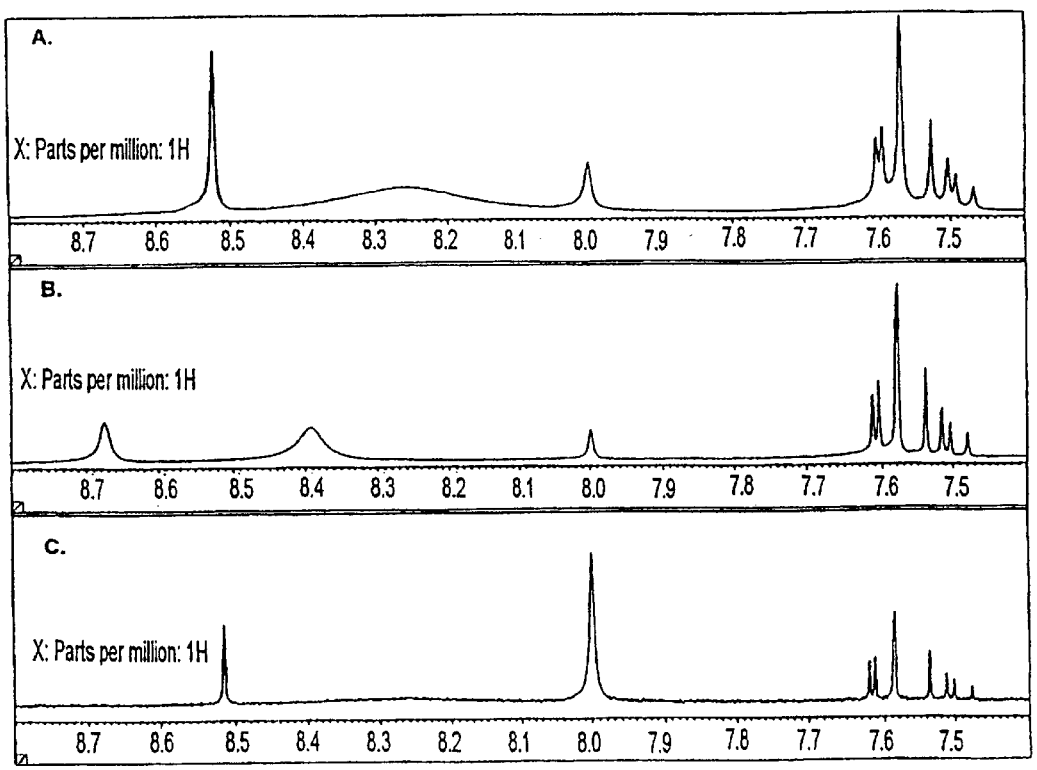
FIG. 2 shows NMR spectroscopy of guanabenz, guanoxabenz and the HPLC purified product formed upon incubation of guanoxabenz with spleen cytosol.

The compound obtained after HPLC purification was analysed using $^1$H-NMR spectroscopy and the results from these tests are shown in FIG. 2. For both guanabenz and guanoxabenz the typical pattern for a symmetrical 1,2,3-trisubstituted aromatic was obtained. For guanabenz, a broad signal is observed over the range 7.9–8.7 ppm, while for guanoxabenz a broad signal appears over the range 7.35–7.45. Whilst these signals are clearly different they are too broad to be used for the definite assignment of a small sample. The signals assigned to the imine protons appear as sharp singlets at 8.68 ppm for guanoxabenz and 8.52 ppm for guanabenz. Since these signals are well defined and appear reasonably well separated they may be used for the assignment of the structure of the product. The $^1$H-NMR of the sample of enzymatic origin showed a sharp singlet at 8.513 ppm allowing for confirmation of the structure as that of guanabenz.

The details for FIG. 2 are as follows: Shown in FIG. 2 is the region of the 270 MHz $^1$H-NMR spectra from 7.4–8.8 ppm of, in A. 0.095 M guanabenz in N,N-dimethylformamide-D7, B. 0.090 M guanabenz in N,N-dimethylformamide-D7 and in C. approximately 0.01 M of the product obtained from enzymatic treatment of guanoxabenz in N,N-dimethylformamide-D7.

EXAMPLE 2

Method for assaying hydroxyguanidine reducing activity

Some of the hydroxyguanidine analogues used for development of the present invention showed activity for α2-adrenergic receptors. Since for these cases the affinity of the reduced product for the α2-adrenoceptor was generally substantially different than it was for the native hydroxyguanidine, this made possible a convenient assay for estimating the conversion of the hydroxyguanidine to the corresponding guanidine. In particular the hydroxyguanidine guanoxabenz was used in these assays because its reduction product, guanabenz, shows substantially higher affinity for α2-adrenoceptors compared to guanoxabenz itself. The α2-adrenoceptors used in these assays were obtained from either human HT29 cell, or from the brains of rats, as is described below.

Preparation of membranes for bioassay of hydroxyguanidines and their products

Preparation of HT29 membranes. HT29 cells were grown in DMEM medium supplemented with 10% foetal calf serum, 100 units/ml penicillin and 100 μg/ml streptomycin at 37° C. under 5% $CO_2$ in 75 $cm^2$ Costar cell culture flasks. Cell membranes were prepared by rinsing the HT29 cells twice with PBS containing 2 mM Tris-Cl, 1 mM EDTA. The cells were then scrapped of the plates into 5 ml of same buffer. The cells were then homogenized by using an Ultra-Turrax homogenizer (IKA T25, equipped with an 8 mm diameter probe). The homogenate was centrifuged at 600×g for 5 min, the supernatant was decanted and then centrifuged at 30,000×g for 15 min at 4° C. in a Beckman J2-21 centrifuge. The resulting pellet was re-suspended in 50 mM Tris-Cl, 1.5 mM EDTA and stored frozen at −80° C. until further used.

Preparation of rat cerebral cortex membranes. Male Sprague-Dawley rats weighing 200–300 grams were decapitated and the cerebral cortices were rapidly excised and homogenized in icecold 50 mM Tris-Cl, 5 mM EDTA, 0.1 mM PMSF (phenyl methyl sulphonyl fluoride), 10 μg/ml soybean trypsin inhibitor and 200 μg/ml bacitracin, pH 7.5, using a motor driven teflon glass homogenizer. The homogenates were spun at 500×g and the supernatants collected and spun at 38,000×g for 12 minutes. The pellets were twice resuspended and recentrifuged in 1.5 mM EDTA, 50 mM Tris-Cl pH 7.5. The final pellets were diluted to protein concentrations of about 2.4 mg protein/ml with 1.5 mM EDTA, 50 mM Tris-Cl pH 7.5. Aliquots of the membranes were frozen and stored at −80° C. until used.

Assay of hydroxyguanidine reducing activity by radioligand binding. The assay is based on the possibility to measure the affinity of ligands to α2-adrenoceptors by using radioligand binding. In a typical experiment small aliquots of the sample to be measured is added to an assay containing membranes rich in α2-adrenoceptors as well as a suitable concentration of a radioligand capable of binding to α2-adrenoceptors. After the assay mixture has been incubated for a suitable time, to achieve equilibrium, the amount of radioligand bound to the membranes is measured by washing and filtering on GF/C glass fibre filters using methods that are well described in literature, and which are commonly referred to as radioligand binding. The ability of the hydroxyguanidine and its product to inhibit the binding of the radioligand to the α2-adrenoceptor constituted a measure of the hydroxyguanidine/guanidine activity of the reaction mixture. A preferred hydroxyguanidine is one which corresponding guanidine show substantially different affinity compared to the hydroxyguanidine itself. A most preferred example of such a hydroxyguanidine is guanoxabenz.

In the standard version of the assay the hydroxyguanidine reducing activity is estimated by adding a constant amount of guanoxabenz to an assay mixture containing the activity to be measured. After completion of the reaction the reducing activity is estimated by adding aliquots of the assay mixture to a radioligand assay with the purpose to estimate the α2-adrenoceptorbinding activity of the reaction mixture.

In a simplified version of the above assay the relative change of α2-adrenoceptor binding activity is estimated by adding a single dilution of the aliquot to the binding assay, and then comparing this activity of the activity of an aliquot obtained from a blank assay that did not contain hydroxyguanidine reducing activity.

In a more more exact version of the assay the "apparent affinity" of the mixture of hydroxyguanidine and guanidine-product is measured by constructing a complete competition curve for each sample to be measured. This is achieved by adding different dilutions of the reaction mixture to the radioligand binding assay. Since the sum of the concentration of the hydroxyguanidine and the guanidine product is known, the "apparent affinity" of the mixture can be calculated from the radioligand binding data using standard procedures for radioligand binding data analysis (Uhlén and Wikberg,1991). For the purpose of the present studies the apparent affinity of the reaction mixture was estimated from competition data by using a radioligand binding analysis computer software package (Wan System AB, Trillvägen 13, S-905 92 Umeå, Sweden). The fraction (q) of guanidine product obtained is then given by:

$$q = \frac{[P]}{[S]+[P]} = \frac{Kp(Ks-Km)}{Km(Ks-Kp)}$$

where [P] is the concentration of the product in the reaction mixture at completion of the reaction, [S] the concentration of the substrate in the reaction mixture at completion of the reaction, [S]+[P] the sum of the concentration of substrate and product at the completion of the reaction, which corresponds to the concentration of the substrate added into the reaction mixture upon the initiation of the reaction, Kp the known dissociation constant of the product for the α2-adrenoceptor, Ks the known dissociation constant of the substrate for the α2-adrenoceptor and Km the apparent dissociation constant of the mixture for the α2-adrenoceptor. When q has been determined the concentration of the enzymatic reaction product [P] can be calculated from the formula:

$$[P]=q[S0]$$

where [$S_0$] is the initial concentration of hydroxyguanidine present in the reactive mixture (i.e. at time zero).

In a typical assay the α2-adrenoceptor containing membranes (from HT29 cells or rat cerebral cortex) were used, and the α2-adrenoceptor binding activity measured by using the α2-adrenoceptor radioligand [$^3$H]RX821002 (Amersham, Buckinghamshire, UK).

The dissociation constant of the substrate and product, $K_s$ and $K_p$, were measured separately in competition studies using the native compounds, and [$^3$H]RX821002 by applying standard procedures for radioligand binding analysis (Uhlén and Wikberg, 1991) and performing calculations on the resulting data using the radioligand data analysis programme.

An exemplary application of the method was the use of guanoxabenz, which reduction product is guanabenz. For guanoxabenz the $K_s$ was estimated to be 4000 nM and for the reduction product $K_p$ was 25 nM.

Figure 3:
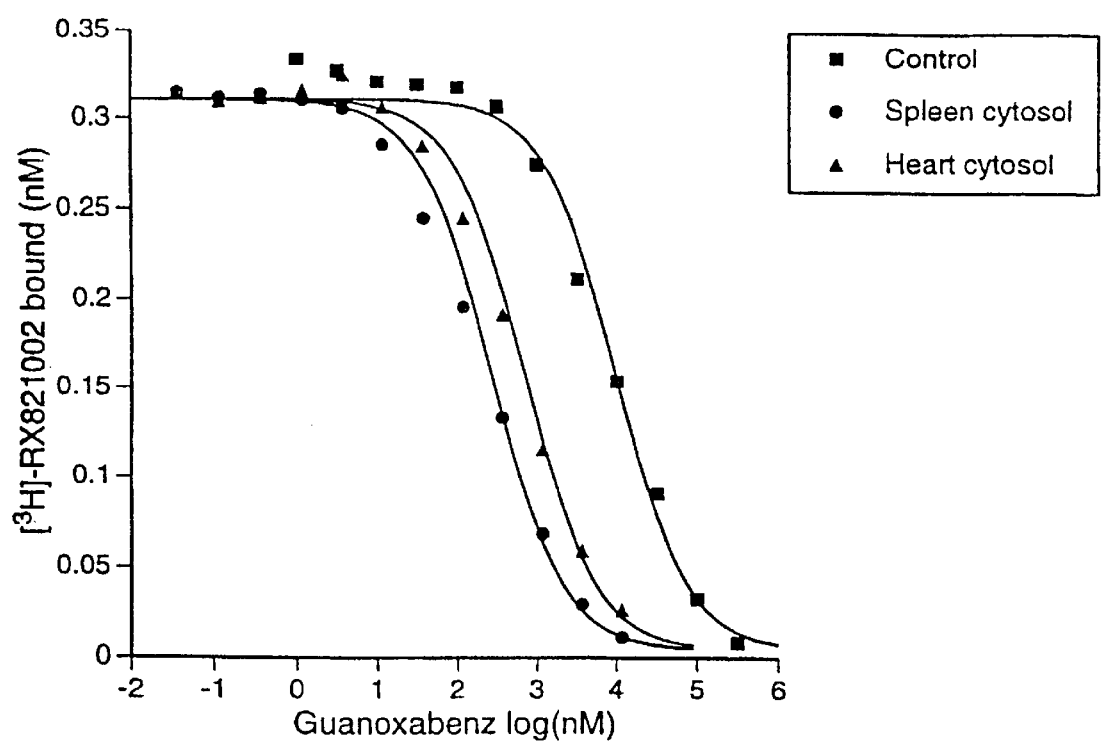
FIG. 3 shows radioligand binding assay of hydroxyguanidine reducing activity.

FIG. 3 show exemplary results for the assay of two different samples containing unknown proportions of guanoxabenz and its reduction product guanabenz. For the purpose of these tests 70 μM guanoxabenz was first incubated with either rat spleen or rat heart cytosol that had been diluted with 25 mM Tris, 0.75 mM EDTA, 0.25 mM DTT, 1 mM $MgCl_2$, pH7.5. (In these tests the tissue cytosols were prepared essentially as described in Example 1 for the preparation of rat spleen cytosol). As a control served as incubation in which the tissue cytosol had been excluded. Incubations were for 1 hr at 25° C. whereafter reactions were stopped by heating to 80° C. for 5 min. The samples were then centrifuged to remove denatured protein, and the resulting supernatants subjected to measurement of the Km using cerebral cortex membranes, [$^3$H]RX821002 and adding different dilutions of the test sample to the radioligand assay using a standard radioligand binding assay protocol (Uhlén and Wikberg, 1991). As can be seen from FIG. 3 both heart and spleen cytosol induced a drastic increase in apparent affinity of guanoxabenz. For the test of heart cytosol the $K_m$ was estimated to 259 nM, which corresponds to a q=0.09 (i.e. 9% conversion of guanoxabenz to guanabenz; the concentration of guanabenz in the sample being 6.3 $\mu$M). For the test of spleen cytosol the $K_m$ was estimated to be 99.5 nM which corresponds to a q=0.25 (i.e. 25% conversion of guanoxabenz to guanabenz; the concentration of guanabenz in the sample being 17.5 $\mu$M).

In a simplified form of the assay the α2-adrenoceptor containing membranes and the [$^3$H]RX821002 radioligand were added together with the hydroxyguanidine reducing activity and the hydroxyguanidine, and the mixture then incubated for a suitable time. In this implementation of the assay the reduction of the hydroxyguanidine occurred simultaneously with the assay of the $K_m$. Example of this variant of the assay is given in Examples 4 and 8.

EXAMPLE 3

Purification of a hydroxyguanidine reducing activity from spleen cytosol and identification of activity as being the xanthine dehydrogenase/xanthine oxidase enzyme Preparation of spleen cytosol. Rat spleens were homogenised (1:10 w/v) in ice-cold 20 mM Tris, 1.5 mM EDTA, pH 7.5 with glass/Teflon homogenizer. The homogenate was centrifuged at 30,000×g for 15 min at 4° C. in a Beckman J2-21 centrifuge and stored frozen at −80° C. After thawing the supernatant was centrifuged at 70,000×g for 1 hr in a ultracentrifuge at 4° C.

Enzyme activity assay. Enzymatic activities were estimated as described in Example 2.

Purification procedure. All purification procedures were conducted at 0–4° C. The ultracentrifuge supernatant was first loaded onto a DEAE Sepharose CL-6B column pre-equilibrated with 20 mM Tris, 1.5 mM EDTA, pH 7.5 and the unbound protein washed away with a large volume of the same buffer until no absorbance at 280 nm was detectable in the eluate. Protein was then eluted with a linear gradient created by 0–400 mM NaCl added to the same buffer as above and 10 ml fractions were collected. A single peak of hydroxyguanidine reducing activity was eluted by about 100 mM NaCl. The fractions containing activity were pooled and directly loaded onto a BioRad Macro-Prep Ceramic Hydroxyapatite column that had been equilibrated with 100 mM potassium phosphate buffer (pH 7.5). The hydroxyapatite column was eluted with a linear gradient 100–400 mM of K-phosphate buffer which resulted in the elution of a single peak of enzyme activity close to 400 mM potassium phosphate. The fractions showing activity were pooled and concentrated in a Millipore Ultrafree-15 Centrifugal filter device (Biomax 30 membrane) to a final volume about 1 ml. Aliquots of 200 $\mu$l of this concentrate were applied to a Superdex 200 HR 10/30 column and eluted with 20 mM Tris, 1.5 mM EDTA (pH7.5). The fractions containing hydroxyguanidine reducing activity were pooled, concentrated 10-fold by using the Millipore Ultrafree-15 Centrifugal filter device and then reapplied to Superdex 200 HR 10/30 column. In the second Superdex −200 run a single symmetric UV absorbing peak showing enzymatic activity was eluted. These fractions were again pooled, concentrated and stored at −80° C. until analysed further.

Gel electrophoresis. The purity of the final enzyme preparation was checked by nondenaturing polyacrylamide gel electrophoresis (PAGE) using a 6% gel. On this gel one major band was visible after Coomasie Blue or silver staining. The molecular mass of the purified protein was estimated to be 450 kDa.

Protein sequence analysis. The purified enzyme was electrophorized on 8% SDS-polyacrylamide gels according to the method of Laemmli (1970). Prior to application to the gel the material was boiled in the sample buffer. After the electrophoresis protein bands were transferred to a PVDF Protein Sequencing Membrane (BioRad). The PVDF membrane was stained with Commasie blue, bands cut out and subjected to N-terminal amino acid sequence analysis using automated Edman degradation sequence analyser. From one major band, that corresponded to a molecular mass of 102 kDa a sequence of eight amino acids was obtained: ANVQLFQE. A SwissProt database search revealed that this sequence matched eight residues of rat xanthine dehydrogenase (EC 1.1.1.204) and xanthine oxidase (EC 1.1.3.22), beginning at residue 543 of the published sequence (Amaya et al., 1990). It was therefore concluded that the 102 kDa band was a fragment derived from the xanthine dehydrogenase/xanthine oxidase enzyme.

EXAMPLE 4

Figure 4:
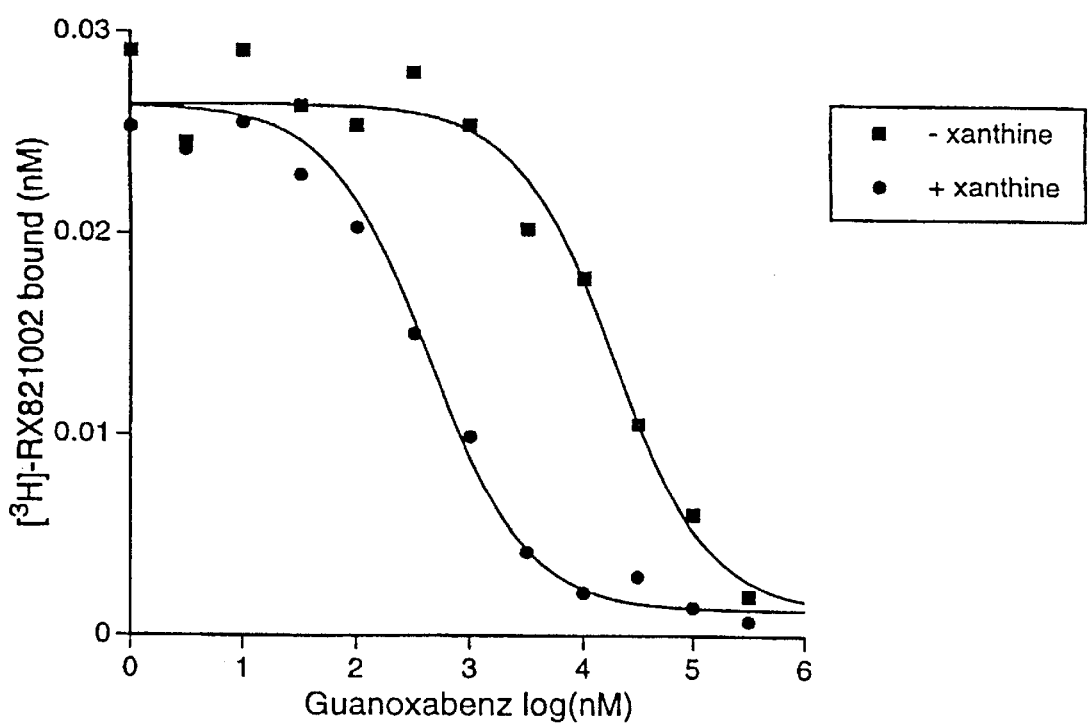
FIG. 4 shows radioligand binding assay of hydroxyguanidine reducing activity of bovine xanthine oxidase.

Hydroxyguanidine reducing activity of bovine xanthine oxidase. A hydroxyguanidine reducing activity of bovine xanthine oxidase was demonstrated by adding varying concentrations of guanoxabenz to yield an assay mixture of 150 $\mu$l volume that contained 0.004 units/ml of bovine milk xanthine oxidase (Sigma, St. Louis, Mo., USA), 100 $\mu$M xanthine, 50 pM α2-adrenoceptors (in HT29 cell membranes), 33 mM Tris HCl, 1 mM EDTA, pH 7.5, and incubating for 1 hour at 25° C. As a control served a reaction mixture of the same composition, except that xanthine had been omitted. The reaction was stopped by filtrating and washing with 20 ml of ice-cold 50 mM Tris buffer (pH 7.5) on GF/C glass fibre filters and the filters then subjected to radioactivity counting. In FIG. 4 exemplary details of the results obtained from such an assay are shown. As can be seen from FIG. 4 the addition of xanthine to the assay lead to an about 40-fold increase in the apparent affinity of guanoxabenz compared to the case when xanthine was absent. The aperent Kd value of guanoxabenz in the absence of xanthine in these tests estimated to be 8800 nM, and in the presence of xanthine 204 nM. These readings corresponded to a none of the guanoxabenz being converted to guanabenz in the absence of xanthine, and to an about 88% conversion in the presence of xanthine.

EXAMPLE 5

Figure 5:
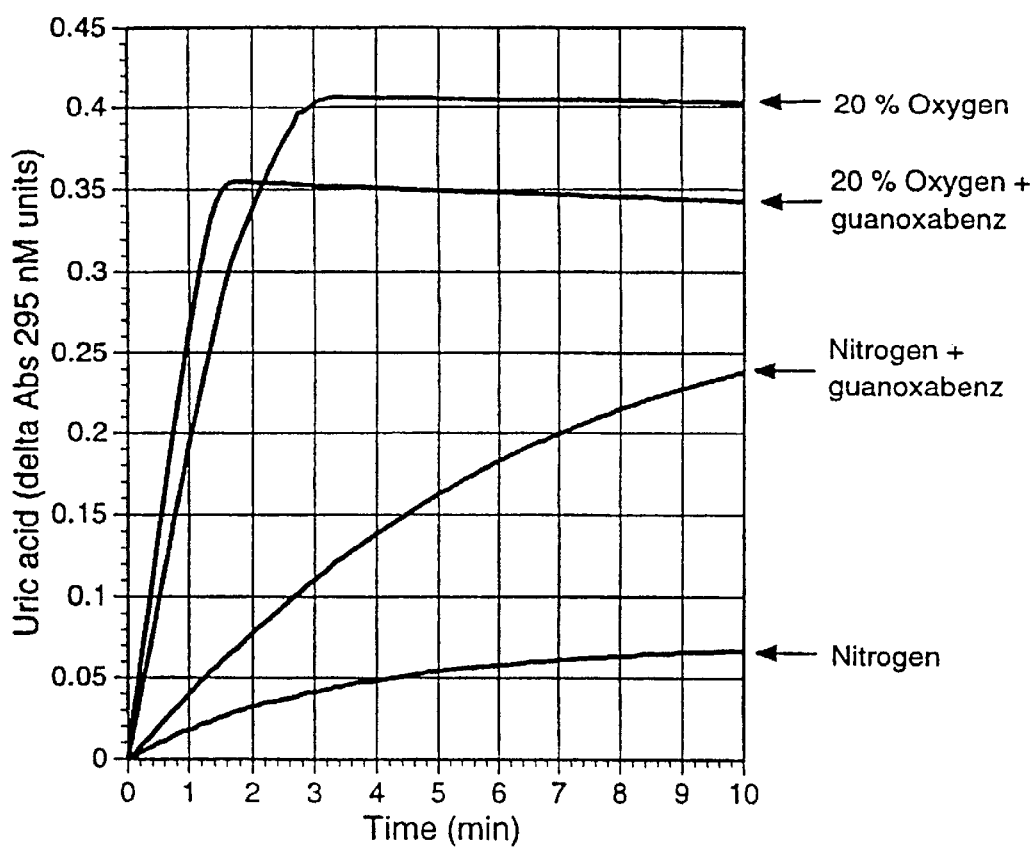
FIG. 5 shows oxidation of xanthine to uric acid by bovine xanthine oxidase.

Capacity of hydroxyguanidines to sustain oxidation of xanthine by xanthine oxidase in the absence and in the presence of oxygen. The capacity of hydroxyguanidines to sustain the oxidation of xanthine to uric acid in the absence and presence of oxygen was assayed by using a spectrophotometric method. In this method bovine milk xanthine oxidase was injected to a Helma® sealable cuvette for anaerobic applications thereby creating 1 ml of a reaction mixture that contained reagents as follows: 50 $\mu$M of a hydroxyguanidine, 50 $\mu$M xanthine, 0.05 units/ml bovine milk xanthine oxidase, 50 mM Tris and 1.5 mM EDTA; the pH of the reaction mixture being 7.5, and the temperature being 20° C. Anaerobic conditions were assured by pre-gassing all solutions used for 5–10 min, with nitrogen whereas aerobic conditions was assured by exposing the solutions to air. The rate of formation of uric acid was monitored spectrophotometrically by measuring the increase in absorbance at 295 nm (the absorption maximum for uric acid) at timed intervals. In FIG. 5 are shown examplary recordings from these tests. In this test the hydroxyguanidine was guanoxabenz. As can be seen from the figure the addition of guanoxabenz results in a substantial increase in the rate of the formation of uric acid both in the absence of oxygen (i.e. nitrogen) as well as in the presence of 20% oxygen.

EXAMPLE 6

Figure 6:
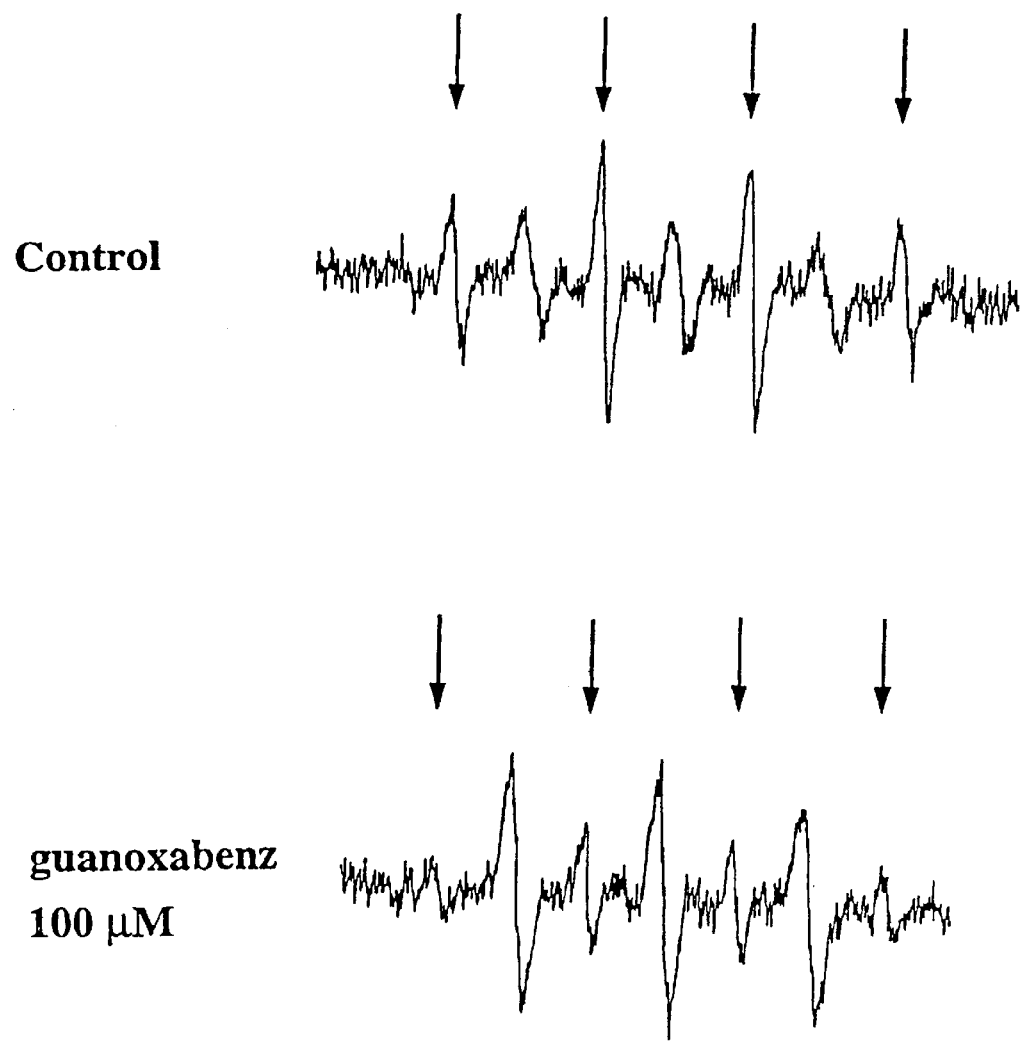
FIG. 6 shows inhibition of xanthine oxidase promoted superoxide radical formation by guanoxabenz through EPR spectra.

Capacity of hydroxyguanidines to inhibit the formation of superoxide radicals by xanthine oxidase in the presence of oxygen. The detection of the spin adducts of superoxide formed by xanthine oxidase and xanthine reaction was performed by using a Bruker ER200D-SRC EPR spectrometer equipped with an ER4105ST double cavity and the spin trap agent DMPO, by essentially using the approach described by Britigan et al. (1990). In brief, reaction mixtures of total volumes of 0.5 ml were prepared by adding to a plastic tubes, in the listed order, reagents that gave final concentrations as follows: 50 mM Tris HCl, 1.5 mM EDTA, 100 $\mu$M xanthine, 100 $\mu$M guanoxabenz, 0.04 units/ml xanthine oxidase and 50 $\mu$M DMPO, pH 7.5. As a control served an identical reaction mixture except that guanoxabenz had been omitted. The solutions were immediately transferred to standard flat cells for aqueous samples and spectra were recorded at room temperature. Spectrometer settings were as follows: microwave power 3.99 mW; modulation amplitude 1.028 G; time constant 10.24 ms; modulation frequency 100 kHz; receiver gain, $5\times10^4$. In FIG. 6 is shown an exemplary recording from these tests. As can be seen from the figure the EPR spectra demonstrated a four line 1:2:2:1 signal (indicate by arrows in FIG. 6) corresponding to superoxide. Moreover as can be seen from the figure the presence of 100 $\mu$M guanoxabenz resulted in about 60% reduction of the superoxide signal thus demonstrating the capacity of guanoxabenz to inhibit the formation of superoxide. As can be seen from the figure the EPR spectra contained additional three line 1:1:1 signal. This additional signal was due to a contaminant corresponding to "nitric oxide" that was released from the disposable laboratory plastic used in the preparation of the samples (see Buettner et al., 1991).

EXAMPLE 7

Capacities of a series of hydroxyguanidine to sustain the oxidation of xanthine by xanthine oxidase in the absence of oxygen. The capacities of various hydroxyguanidines to sustain the oxidation of xanthine was assayed by using a spectrophotometric method. In this method bovine milk xanthine oxidase was injected to a Helma® sealable cuvette for anaerobic application thereby creating 1 ml of a reaction mixture that contained reagents as follows: 50 $\mu$M of a hydroxyguanidine, 50 $\mu$M xanthine, 0.05 units/ml bovine milk xanthine oxidase, 50 mM Tris and 1.5 mM EDTA; the pH of the reaction mixture being 7.5, and the temperature 20° C. Anaerobic conditions were assured by pre-gassing all solutions used for 5–10 min, with nitrogen. The rate of formation of uric acid was monitored spectrophotometrically by measuring the increase in absorbance at 295 nm (the absorption maximum for uric acid) at intervals. The relative capacities of the hydroxyguanidines to sustain oxidation of xanthine were estimated from the derivative of the initial linear phase of the curves. To obtain blank readings an equal volume of the solvent of the hydroxyguanidine (water) was added to the reaction mixture in separate experiments and the initial rate of absorbance change was substracted from the rate readings of the tested hydroxyguanidine. Exemplary hydroxyguanidines tested according to this method are shown in Table 1 (see following pages).

Figure 7:
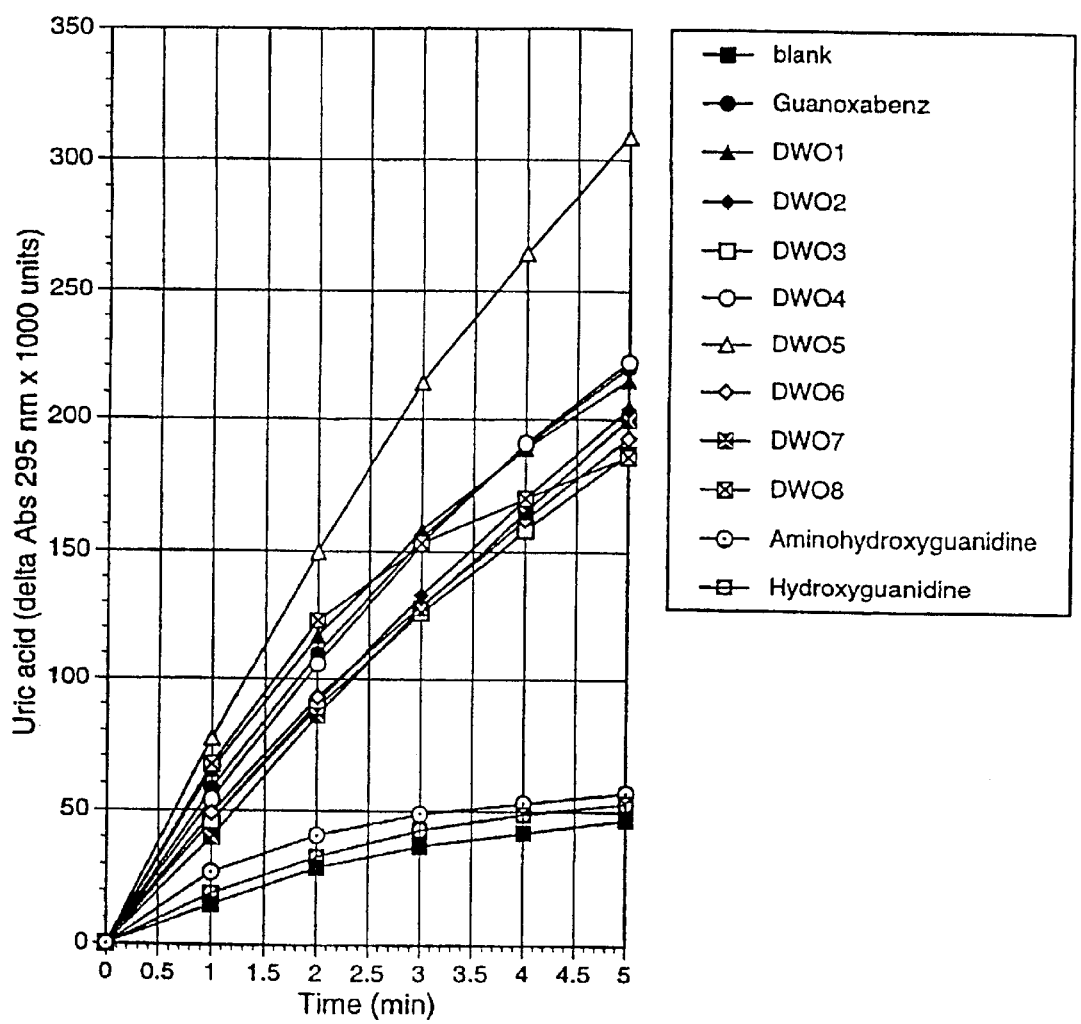
FIG. 7 shows oxidation of xanthine to uric acid sustained by hydroxyguanidines.

The relation between change of absorbance with time for some of the exemplary hydroxyguandines listed above are given in FIG. 7. As can be seen from FIG. 7 there is a wide variation in the capacity of various hydroxyguanidines to support the oxidation of xanthine by xanthine oxidase.

Exemplary initial rates for the rate of the support of the oxidation of xanthine obtained by assaying the exemplary hydroxyguanidines listed above by the method in the present example are furthermore given in Table 2:

TABLE 2

| Test compound | V = 1000 × ($\Delta$abs 295 nm) min$^{-1}$ |
|---|---|
| Hydroxyguanidine | 0.7 |
| Aminohydroxyguanidine | 1.4 |
| DWO3 | 29.4 |
| DWO7 | 30.7 |
| DWO6 | 30.7 |
| DWO2 | 30.7 |
| DWO4 | 36.7 |
| DWO1 | 40 |
| Guanoxabenz | 40 |
| DWO8 | 45.4 |
| DWO5 | 59.7 |
| LW01 | 0 |
| LW04 | 55 |
| LT5 | 50 |
| LT7 | 12 |
| LT10 | 3 |
| LT11 | 26 |
| PR1 | 63 |
| PR2 | 1 |
| PR4 | 7 |
| PR5 | 96 |
| PR6 | 4 |
| PR8 | 29 |
| PR10 | −1 |
| PR11 | 12 |
| PR12 | 11 |
| PR13 | 3 |
| PR14 | 14 |
| PR15 | 7 |
| PR16 | 13 |
| PR17 | −2 |
| PR18 | 43 |
| PR19 | 5 |
| PR20 | 13 |
| PR21 | 5 |
| EN10 | 22 |
| EN12 | 11 |
| EN18 | 5 |
| EN16 | 66 |
| EN20 | 44 |

Sources of known compounds. Hydroxyguanidine: Pfalz & Bauer, Inc.; CT, USA. Aminohydroxyguanidine (1-amino-3-hydroxyguanidine) was prepared according to Canadian Patent No. 894 265. Compounds termed "DWO" were prepared according to Doubell & Oliver, Drug Res., 1992, 42, 65–69. Guanoxabenz was prepared according to Ledoux et al. Therapie, 1981, 46(2), 187–191. LW01 and LW04 were prepared according to Wang et al., J. Med. Chem. 1990, 33, 608–614. LT5, LT7, LT10 and LT11 were prepared according to Tai et al., J. Med. Chem., 1984, 27, 236–238. PR and EN compounds were prepared as described in Example 11.

TABLE 1
| Structure | Name |
|---|---|
| 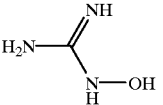 | Hydroxyguanidine (8) |
| 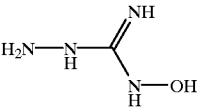 | Aminohydroxyguanidine (9) |
| 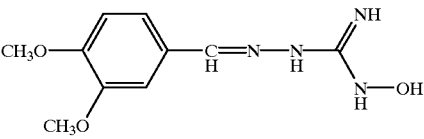 | DW01 (10) |
| 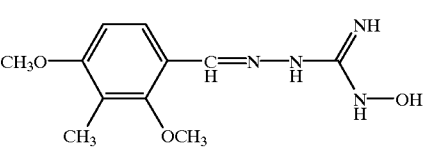 | DW02 (11) |
| 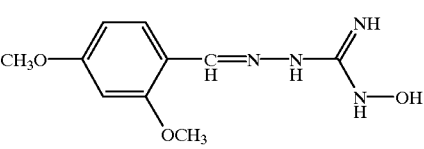 | DW03 (12) |
| 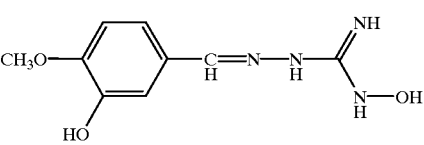 | DW04 (13) |
| 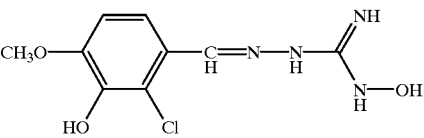 | DW05 (14) |
| 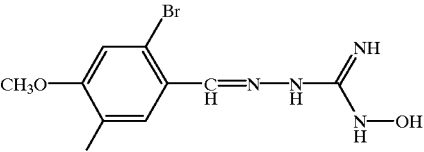 | DW06 (15) |
| 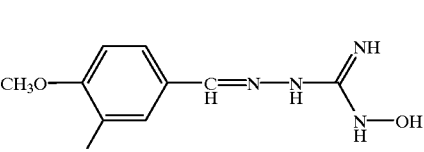 | DW07 (16) |
| 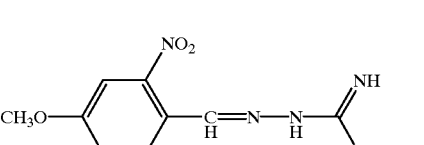 | DW08 (17) |

TABLE 1-continued
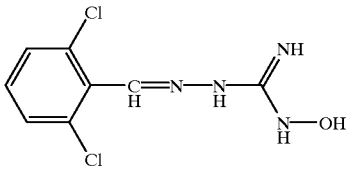 Guanoxabenz (3)
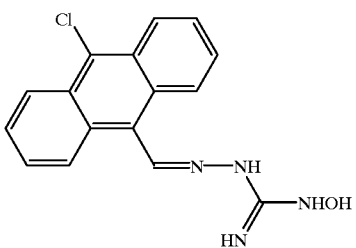 LW01 (18)
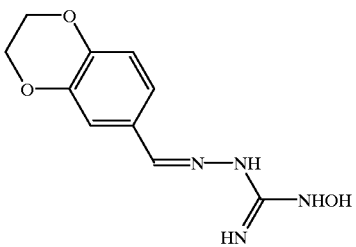 LW04 (19)
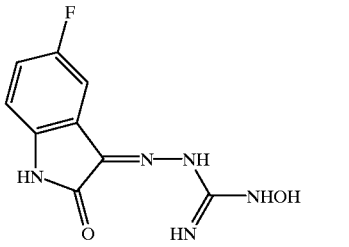 LT5 (20)
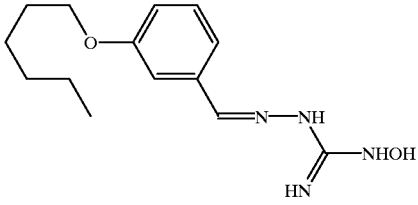 LT7 (21)
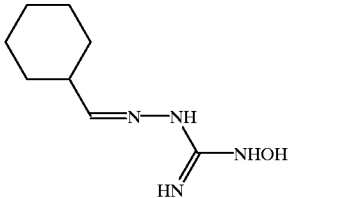 LT10 (22)

TABLE 1-continued

| Structure | Label |
|---|---|
| (3-methoxyphenyl)-CH=N-NH-C(=NH)-NHOH | LT11 (23) |
| HOHN-C(=NH)-NH-N=CH-(1,4-phenylene)-CH=N-NH-C(=NH)-NHOH | PR1 (24) |
| (Ph)₂C=N-NH-C(=NH)-NHOH | PR2 (25) |
| cyclohexylidene=N-NH-C(=NH)-NHOH | PR4 (26) |
| (2-chloro-3,4-dimethoxyphenyl)-CH=N-NH-C(=NH)-NHOH | PR5 (27) |
| (1H-1,2,4-triazol-5-yl)-NHOH | PR6 (28) |
| HOHN-C(=NH)-NH-N=CH-(1,3-phenylene)-CH=N-NH-C(=NH)-NHOH | PR8 (29) |
| (CH₃)₂CHCH₂CH=N-NH-C(=NH)-NHOH | PR10 (30) |

TABLE 1-continued
| | |
|---|---|
| 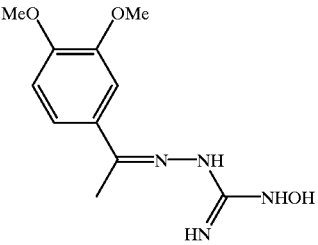 | PR11 (31) |
| 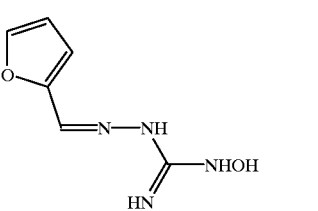 | PR12 (32) |
| 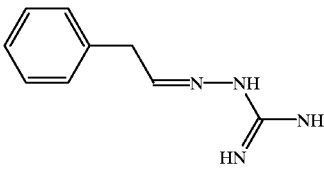 | PR13 (33) |
| 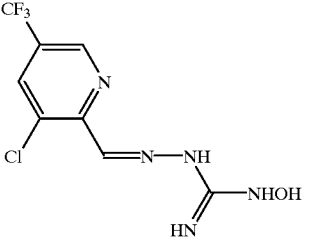 | PR14 (34) |
| 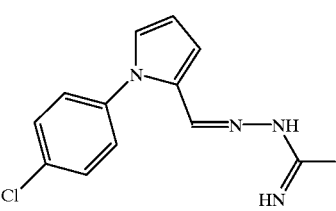 | PR15 (35) |
| 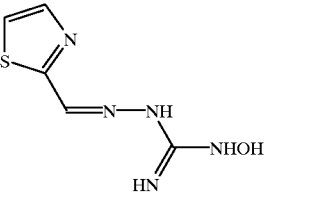 | PR16 (36) |
| 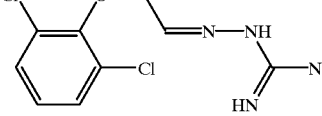 | PR17 (37) |

TABLE 1-continued
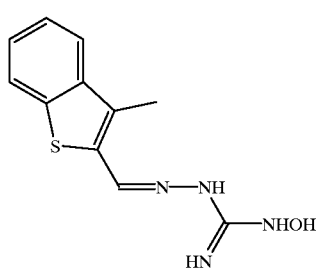 PR18 (38)
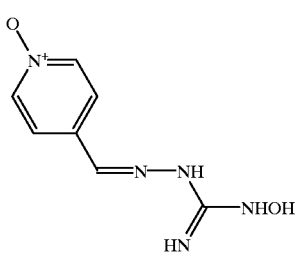 PR19 (39)
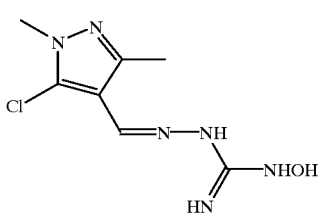 PR20 (40)
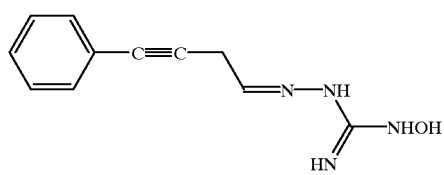 PR21 (41)
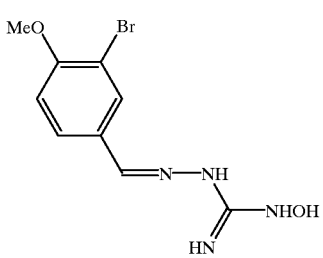 EN10 (42)
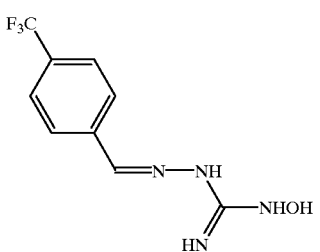 EN12 (43)
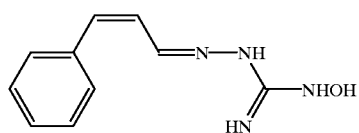 EN16 (44)

TABLE 1-continued

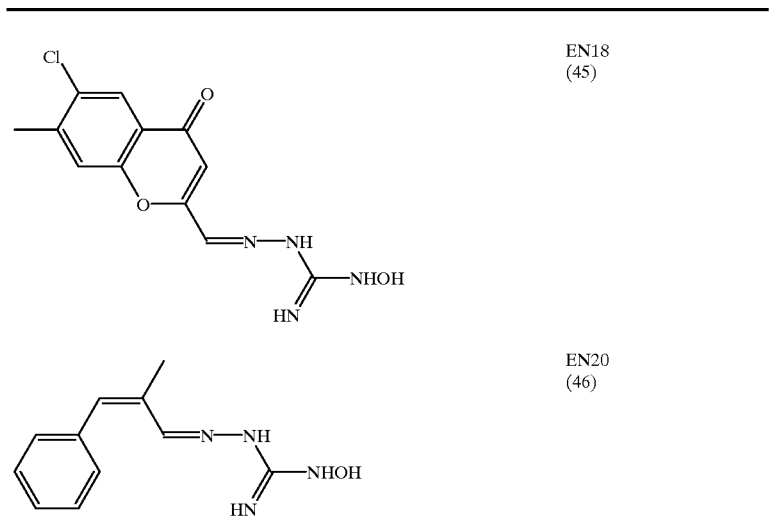

EN18
(45)

EN20
(46)

EXAMPLE 8

Figure 8:
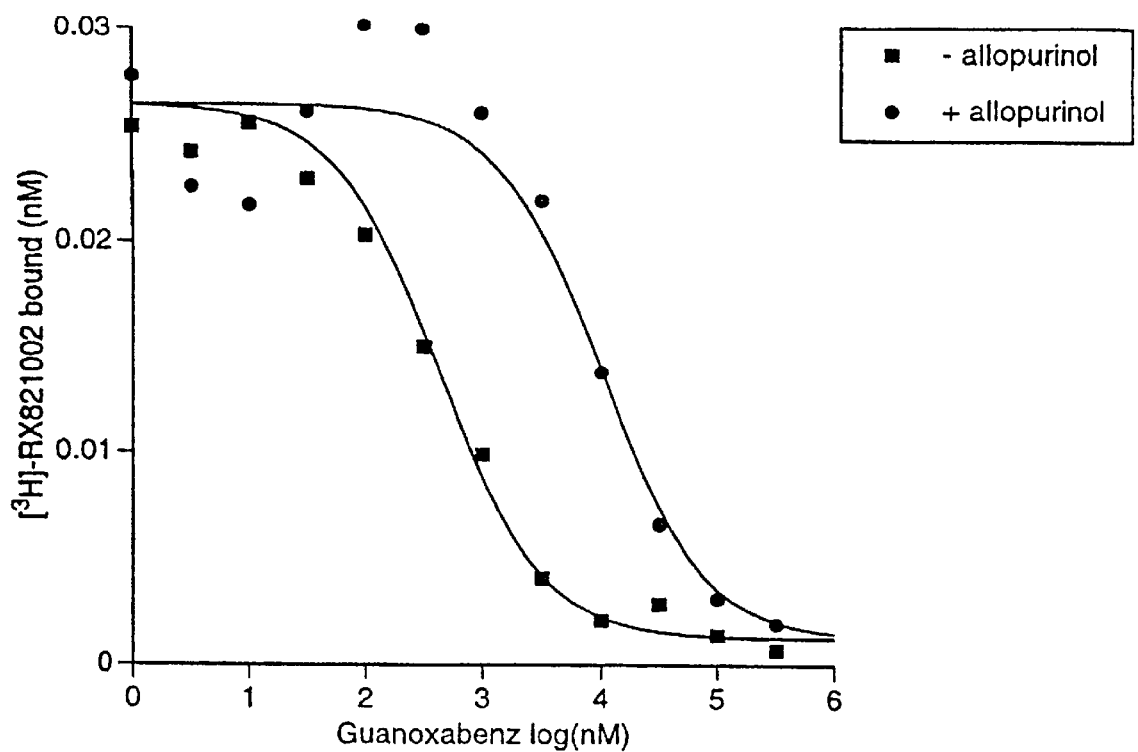
FIG. 8 shows inhibition of hydroxyguanidine reducing activity of bovine xanthine oxidase by allopurinol in a radioligand binding assay.

Capacity of allopurinol to inhibit the reduction of hydroxyguanidines by xanthine oxidase. In order to demonstrate the capacity of allopurinol to inhibit the reduction of hydroxyguanidines a protocol essentially as described in Example 4 was used. In these tests varying amounts of guanoxabenz was added to assays yielding 150 µl final volumes and containing final concentrations 0.004 units/ml of bovine milk xanthine oxidase (Sigma, St. Louis, MO., USA), 100 µM xanthine, 20 µM allopurinol, 50 pM α2-adrenoceptors (in HT29 cell membranes), 33 mM Tris HCl, 1 mM EDTA, pH 7.5, and incubating for 1 hour at 25° C. As a control served a reaction mixture of the same composition, except that allopurinol had been omitted. The reaction was stopped by filtrating and washing with 20 ml of ice-cold 50 mM Tris buffer (pH 7.5) on GF/C glass filters, and the filters were then subjected to radioactivity counting. In FIG. 8 exemplary details of the results obtained from such assays are shown. As can be seen from FIG. 8 the addition of allopurinol lead to an about 24-fold decrease in the apparent affinity of guanoxabenz compared to the case when allopurinol was absent. The aparent $K_d$ value of guanoxabenz in the absence of xanthine was in these tests estimated to be 4900 nM, and in the presence of xanthine 204 nM. These readings corresponded to none of the guanoxabenz being converted to guanabenz in the presence of allopurinol, and to an about 88% conversion in the absence of allopurinol. (It should be observed that, in FIG. 8, the "-allopurinol" represent the same data as "+xanthine" in FIG. 4).

EXAMPLE 9

Capacity of a hydroxyguanidine (PR5) to afford a tissue protective effect in the heart. A model for reperfusion injury of the heart was used to demonstrate the tissue protective effect of PR5 essentially according to the method described by Selye et al. (Angiology, 1960, 1, 398–407) and Krzeminski and Chatterjee (Pharm. Pharmacol. Lett., 1993, 3, 45–48). In this model the coronary arteries of rat hearts were occluded, and after some time reperfusion was allowed to occur. During reperfusion events of cardiac arrhythmias are observed. They are well known to be related to the accumulation of oxygen derived free radicals. These arrhythmias are monitored in the animals treated with PR5 and in control animals either receiving no drug or allopurinol. Allopurinol was used as a control because it is well known from the litterature as an agent capable of preventing the generation of oxygen derived free radicals. In brief, rats were anaesthetised with sodium pentobarbital and ventilated with air using a respirator for small animals at a pressure 15–20 cm $H_2O$ and a heart beat rate of 60 strokes/min. ECG (electrocardiogram) and systemic blood pressure was registered on a Physiograph DMP-4B (Narco Bio-Systems, Houston, USA) using, respectively, a standard lead II and a pressure transducer PR-1500 (Narco Bio-Systems, Houston, USA) contected via a catheter to the left carotid artery. The chest was opened via the fourth intercostal space, the pericardium incised and a sling (4/0 silk Medicor, Budapest, Hungary) was placed around the left coronary artery close to its origin. The silk ligature was passed through a piece of plastic tubing, the chest was partially closed and the animal was allowed to recover for 10 min. PR-5, dissolved in 0.9% NaCl, was then injected i.v. 10 min before the occlusion of the coronary artery at doses 1, 3 or 10 mg/kg body weight. As control served the same volume of 0.9% NaCl. The coronary artery was occluded for a period of 10 min by applying tension to the ligature and pressing the tube onto the heart surface. Reperfusion was initiated by removing the clamp and releasing the tension on the ligature and allowing the perfusion to continue for 20 min. Ventricular ectopic activity was assessed during the 20 min reperfusion period by measuring the duration of ventricular tachycardias and ventricular fibrillations from the ECG curves. The results are shown in Table 2, where the results are presented as mean ±SEM (in seconds) for the total duration of ventricular tachycardias and ventricular fibrillations during the 20 min reperfusion period, (or until eventual death of the animal). The incidence of animals showing ventricular tachycardia and ventricular fibrillation are also given Table 2 as the number of animals showing ventricular tachycardia and ventricular fibrillation. Figures in parenthese relate to incidents expressed in % of the total number of animals.

TABLE 2

| Treatment | n | Ventricular tachycardia | | Ventricular fibrilation | | Mortality |
|---|---|---|---|---|---|---|
| | | Insidence (%) | Duration (s) | Insidence (%) | Duration (s) | Insidence (%) |
| Control | 15 | 15 (100) | 89 ± 14 | 14 (93) | 60 ± 16 | 7 (47) |
| PR5 1 mg/kg | 14 | 11 (79) | 61 ± 11 | 8 (57) | 34 ± 9 | 2 (14) |
| PR5 3 mg/kg | 14 | 9 (64) | 38 ± 7* | 6 (43)* | 20 ± 7* | 0 (0)* |
| PR5 10 mg/kg | 14 | 8 (57)* | 34 ± 7* | 5 (36)* | 17 ± 5* | 1 (7)* |
| Alp 10 mg/kg | 14 | 9 (64) | 59 ± 12 | 7 (50)* | 30 ± 10 | 1 (7)* |

In Table 2 a star "*" denotes a significant difference from the control at $p<0.05$ using the appropriate statistical test. Alp=allopurinol. n=number of animals tested. As can be seen from the table PR5 induces a significant decrease in incidence and duration of ventricular tachycardias and fibrillations, as well as a decrease in mortality. Allopurinol 10 mg/kg also reduces these indices, although to a lesser extent than 3–10 mg/kg of PR5.

EXAMPLE 10

Capacity of a hydroxyguanidine (PR5) to sustain the formation of uric acid in tissues. The capacity of PR5 to sustain formation of uric acid in tissues was demonstrated as follows. Pieces of 0.6 g of rat spleen tissue were incubated in 7.5 ml argon-saturated Tris-Ringer buffer (4 mM KCl, 100 mM NaCl, 2 mM $CaCl_2$, 2 mg/ml glucose and 40 mM TrisHCl, pH 7.4) in 50 ml Erlenmeyer flasks at 37° C., care being taken to maintain an atmosphere of argon above the incubations. As aerobic control served identical incubations, except that the buffers were saturated with air and the incubations performed under air. After 30 min the flasks were opened and the tissues minced to obtain tissue cubes with about 1 mm sides. To half of the anaerobic flasks PR5 was then added to achieve a final concentration of PR5 of 0.5 mM, whereas to the other half of the anaerobic flasks the same amount of solvent for PR5 was added, the incubations then being continued for both treatments for additional 60 min under argon. For the aerobic flasks, after the mincing of the tissue, the incubations were continued for further 60 min under air. At the end of the 60 min incubation period the incubation medium, containing the uric acid released from the tissues, were collected by rapidly filtering the incubation mixtures through nylon nets. The filtrates were then immediately boiled at 90–95° C. for 10–15 min and centrifuged at 3000 RPM for 10 min. The supernatants were then centrifuged using Ultrafree-MC Biomax-10 Millipore filtration devices at 5000×g for 0.5 hr in order to obtain an essentially particle free preparation which was being kept at −20° C. until analysed for the uric acid content using HPLC.

For analysing the uric acid content the above preparations were thawed and 0.05 ml aliquots were injected onto Waters 2690 Separation Module using a 2.1×250 mm Vydac RP C18, 90A, 201HS1010 column using a linear gradient of 10 mM $KH_2PO_4$ (A) and 10 mM $KH_2PO_4$ in 50% (v/v) methanol/water (B) (both at pH 4.55 adjusted with phosphoric acid). The flow rate was 0.15 ml/min. A photo diode array detector was used to record chromatographs. The uric acid peak was eluted after 13 min and was identified and detected according to the spectrum of a standard uric acid reference.

The results from these tests were as follows: Aerobic control 285.7 micromol/L, anaerobic control 17.9 micromol/L and PR5 treated anaerobic tissue 285.5 micromol/L of uric acid in original incubation medium.

Thus, these results show that during anaerobic conditions the formation of uric acid is reduced by about 16-fold compared to the aerobic control. However, when PR5 is present under the anaerobic conditions the formation of uric acid is restored completely to that of the aerobic control. Thus, these results show that a hydroxyguanidine, PR5, is capable of sustaining the formation of uric acid in a tissue.

EXAMPLE 11

Synthesis of hydroxyguanidines. The hydroxyguanidines described below under experiments #1–#22 were prepared using the following general method: Equimolar amounts of N-hydroxy-N'-aminoguanidine p-toluenesulphonate or hydrobromide and appropriate carbonyl compound were heated to reflux in ethanol during 0.1–1 h. The reaction was monitored by TLC. After completion the reaction mixture were cooled. In #1 and #5 the product percipitated after cooling. In the other experiments the reaction mixture was concentrated in vacuo and after addition of acetonitrile the product percipitated. In #23 a different method was used as detailed below.

1: 1,4-Bis(N-Hydroxyguanidinoiminomethyl)Benzene Bromide (PR1)

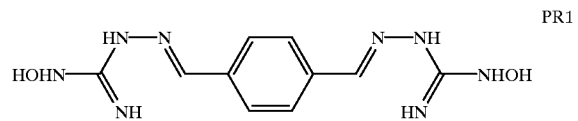

Yield: 80%, m.p. 244–246°. NMR δ(270 MHz, DMSO): 7.93 (4H, s, $C_6H_4$); 8.22 (4H, s, $NH_2$); 8.33 (2H, s, CH); 10.4 (2H, s, NH); 11.4 (2H, s, OH). Found (%): C, 28.9; H, 3.9; N, 26.3. Calculated (%): C, 28.6; H, 3.8; N, 26.7.

2: N-(Diphenylmethyleneamino)-N'-Hydroxyguanidine Bromide (PR2)

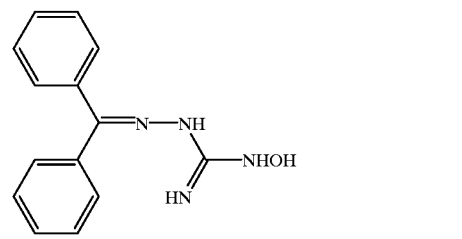

Yield: 55%, m.p. 208–210° C. NMR δ(270 MHz, DMSO): 7.44 (5H, m, $C_6H_5$); 7.67 (5H, m, $C_6H_5$); 8.09 (2H, s, $NH_2$); 9.62 (1H, s, NH); 10.2 (1H, s, NH); 11.2 (1H, s, OH). Found (%): C, 50.7; H, 4.6; N, 17.1. Calculated (%): C, 50.2; H, 4.5; N, 16.7.

3: N-(Cyclohexylideneamino)-N'-Hydroxyguanidine Tosylate (PR4)

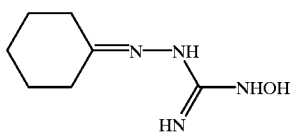

Yield: 53%, m.p. 103–105° C. NMR δ(270 MHz, DMSO): 1.60 (6H, br.s, 3CH$_2$); 2.29 (7H, br.s, CH$_3$ and 2CH$_2$); 7.11 (2H, d, C$_6$H$_2$); 7.49 (2H, d, C$_6$H$_2$); 7.84 (2H, s, NH$_2$); 9.90 (1H, s, NH); 10.4 (1H, s, NH); 10.7 (1H, s, OH). Found (%): C, 49.1; H 6.5; N, 16.6. Calculated (%): C, 49.1; H, 6.5; N, 16.4.

4: N-(3,4-Dimethoxy-2-chlorobenzylideneamino)-N'-hydroxyguanidine tosylate (PR5)

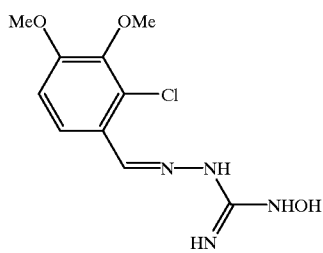

Yield: 95%, m.p. 95–97° C. NMR δ(270 MHz, DMSO): 2.29 (3H, s, CH$_3$); 3.76 (3H, s, CH$_3$); 3.91 (3H, s, CH$_3$); 7.13 (2H, d, C$_6$H$_2$); 7.16 (1H, d, C$_6$H); 7.49 (2H, d, C$_6$H$_2$); 8.09 (1H, d, C$_6$H) 8.22 (2H, s, NH2); 8.58 (1H, s, CH); 10.1 (1H, br.s., NH); 11.3 (1H, br.s., NH); 11.8 (1H, br.s, OH). Found(%): C, 44.6; H, 4.9; N, 11.6. Calculated (%): C, 44.1; H, 5.0; N, 12.1.

5: 1,3-Bis(N-hydroxyguanidinoiminomethyl)benzene tosylate chloride (PR8)

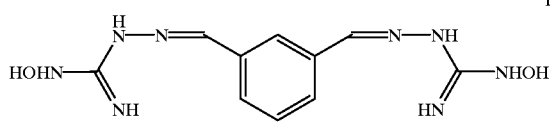

Yield: 48%, m.p. 190–192° C. NMR δ(270 MHz, DMSO): 2.31 (3H, s, CH$_3$); 7.16 (2H, d, C$_6$H$_2$); 7.53 (2H, d, C$_6$H$_2$); 7.55 (1H, s, C$_6$H); 8.00 (2H, d, C$_6$H$_2$); 8.22 (4H, s, NH2); 8.33 (3H, s, CH and C$_6$H); 10.2(2H, s, NH); 11.2 (2H, s, NH); 12.1 (2H, s, OH). Found (%): C, 40.1;H, 4.8; N, 22.5. Calculated (%): C, 40.4; H, 5.0; N, 22.2.

6: N-(3-Methylbutylideneamino)-N'-hydroxyguanidine tosylate (PR10)

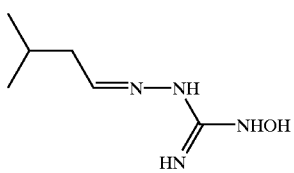

Yield: 46%, m.p. 107–109° C. NMR δ(270 MHz, DMSO): 0.89 (6H, d, CH$_3$); 1.84 (1H, m, CH); 2.12 (2H, t, CH$_2$); 2.28 (3H, s, CH$_3$); 7.11 (2H, d, C$_6$H$_2$); 7.50 (2H, d, C$_6$H$_2$); 7.58 (1H, t, CH); 7.89 (2H, s, NH$_2$); 9.93 (1H, br.s, NH); 10.9 (1H, br.s, NH); 11.2 (1H, br.s, OH). Found (%): C, 46.8; H, 6.7; N, 17.1. Calculated (%): C, 47.3; H, 6.7; N, 17.1.

7: 3,4- Dimethoxyacetophenone-N-hydroxyguanylhydrazone tosylate (PR11)

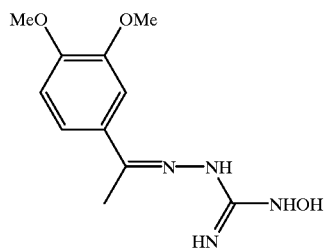

Yield: 60%, m.p. 46–48° C. NMR δ(270 MHz, DMSO): 2.24 (3H, s, CH$_3$); 2.28 (3H, s, CH$_3$); 3.38 (3H, s, CH$_3$); 3.84 (3H, s, CH$_3$); 6.96 (1H, d, C$_6$H$_3$); 7.11 (2H, d, C$_6$H$_4$); 7.40 (1H, d, C$_6$H$_3$); 7.51 (2H, d, C$_6$H$_4$); 7.58 (1H, d, C$_6$H$_3$); 8.1 (2H, s, NH$_2$); 10.2 (1H, br.s, NH); 11.1 (2H, br.s, OH, NH). Found (%): C, 49.7; H, 5.9; N, 13.4. Calculated (%): C, 49.9; H, 5.8; N, 12.9.

190 8: N-(Furyl-2-methyleneamino)-N'-hydroxyguanidine tosylate (PR12)

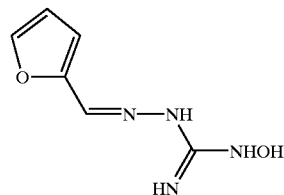

Yield: 60%, m.p. 108–110° C. NMR δ(270 MHz, DMSO): 2.28 (3H, s, CH$_3$); 6.63 (1H, dd, C$_4$HO); 7.05 (1H, d, C$_4$HO); 7.12 (2H, d, C$_6$H$_2$); 7.50 (2H, d, C$_6$H$_2$); 7.83 (1H, d, C$_4$HO); 8.01 (2H, s, NH$_2$); 8.12 (1H, s, CH); 10.2 (1H, br.s, NH); 11.2 (1H, br.s, NH); 11.4 (1H, br.s, OH). Found (%): C, 44.3; H, 4.9; N, 16.2. Calculated (%): C, 44.7; H, 4.9; N, 16.0.

9: N-(Phenylethylideneamino)-N'-hydroxyguanidine tosylate (PR13)

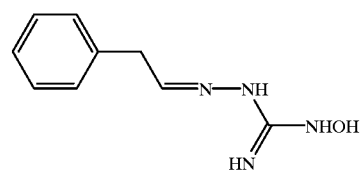

Yield: 60%, m.p. 144–146° C. NMR δ(270 MHz, DMSO): 2.28 (3H, s, CH$_3$); 3.58 (2H, d, CH$_2$); 7.09 (2H, d, C$_6$H$_2$); 7.27 (5H, m, C$_6$H$_5$); 7.47 (2H, d, C$_6$H$_2$); 7.60 (1H, t, CH); 7.94 (2H, s, NH$_2$); 9.94 (1H, br.s, NH); 10.9 (1H, br.s, NH); 11.2 (1H, br.s, OH). Found (%): C, 52.3; H, 5.3; N, 15.0. Calculated (%): C, 52.7; H, 5.5; ,N 15.4.

190 10: N-(3-Chloro-5-trifuluoromethylpyridyl-2-methyleneamino)-N'-hydroxyguanidine tosylate (PR14)

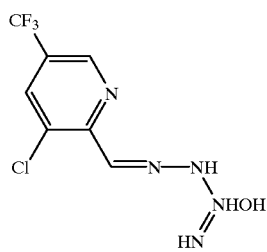

PR14

Yield: 45%, m.p. 162–164° C. NMR δ(270 MHz, DMSO): 2.28 (3H, s, CH₃); 7.09 (2H, d, C₆H₂); 7.49 (2H, d, C₆H₂); 8.20 (2H, s, NH2); 8.49 (1H, s, C₅HN); 8.72 (1H, t, CH); 8.98 (1H, s, C₅NH); 10.3 (1H, br.s, NH); 11.7 (1H, br.s, NH); 11.9 (1H, br.s, OH). Found (%): C, 52.3; H, 5.3; N, 15.0. Calculated (%): C, 52.7; H, 5.5; N, 15.4.

190 11: N-[1-(4-Chlorophenyl)-pyrrolyl-2-methyleneamino(]-N'-hydroxyguanidine tosylate (PR15)

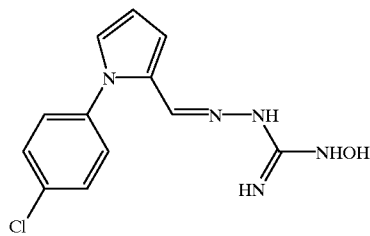

PR15

Yield: 70%, m.p. 126–128° C. NMR δ(270 MHz, DMSO): 2.28 (3H, s, CH3); 6.36 (1H, t, C₄HN); 7.12 (2H, d, C₆H₂); 7.41 (1H, d, C₄HN); 7.49 (2H, d, C₆H₂); 7.61 (1H, d, C₄HN); 7.85 (2H, s, NH₂); 8.05 (1H, s, CH); 9.93 (1H, br.s, NH); 10.8 (1H, br.s, NH); 11.3 (1H, br.s, OH). Found (%): C, 50.2; H, 4.5; N, 16.0. Calculated (%): C, 50.7; H, 4.5; N, 15.6.

12: N-(Thiazolyl-2-methyleneamino)-N'-hydroxyguanidine tosylate (PR16)

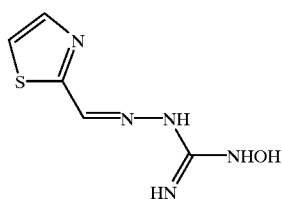

PR16

Yield: 65%, m.p. 165–167° C. NMR δ(270 MHz, DMSO): 2.28 (3H, s, CH₃); 7.12 (2H, d, C₆H₂); 7.52 (2H, d, C₆H₂); 7.89 (1H, d, C₃HNS); 7.97 (1H, d, C₃HNS); 8.23 (2H, s, NH₂); 8.45 (1H, s, CH); 10.2 (1H, br.s, NH); 11.6 (2H, br.s, NH,OH). Found (%): C, 39.8; H, 4.1; N, 19.8. Calculated (%): C, 40.3; H, 4.2; N, 19.6.

13: N-(2,6-Dichlorophenoxyethylideneamino)-N'-hydroxyguanidine bromide (PR17)

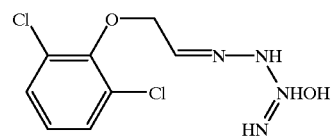

PR17

Yield: 40%, m.p. 134–136° C. NMR δ(270 MHz, DMSO): 4.72 (3H, s, CH₂); 7.14 (3H, m, C₆H₃); 7.94 (1H, t, CH); 8.05 (2H, s, NH₂); 10.1 (1H, br.s, NH); 11.1 (1H, br.s, NH); 11.8 (1H, br.s, OH). Found (%): C 30.4; H 3.1; N 15.8. Calculated (%): C 30.2; H 3.1; N 15.6.

14: N-(3-Methylbenzo[b]thienyl-2-methyleneamino)-N'-hydroxyguanidine tosylate (PR18)

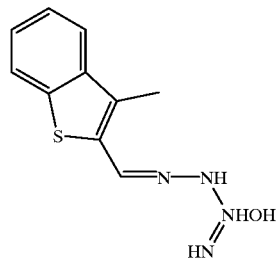

PR18

Yield: 60%, m.p. 123–125° C. NMR d(270 MHz, DMSO): 2.28 (3H, s, CH₃): 2.48 (3H, s, CH₃); 7.12 (2H, d, C₆H₂); 7.32÷8.00 (4H, m, C₈H₄S); 7.54 (2H, d, C₆H₂); 8.05 (2H, s, NH₂); 8.80 (1H, s, CH); 10.3 (1H, br.s, NH); 11.2 (1H, br.s, NH); 11.6 (1H, br.s, OH). Found (%): C, 50.9; H, 4.8; N, 13.7. Calculated (%): C, 51.4; H, 4.8; N, 13.3.

15: N-(N-Oxypyridyl-4-methyleneamino)-N'-hydroxyguanidine tosylate (PR19)

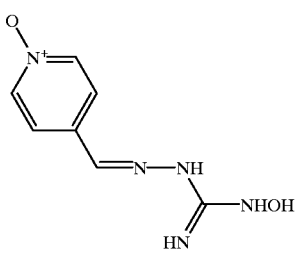

PR19

Yield: 70%, m.p. 133–137° C. NMR δ(270 MHz, DMSO): 2.28 (3H, s, CH3); 7.09(2H, d, C₆H₂); 7.49 (2H, d, C₆H₂); 7.89 (2H, d, C₅H₂N); 8.16 (1H, s, CH); 8.27 (2H, d, C₅H₂N); 8.30 (2H, s, NH₂); 10.2 (1H, br.s, NH); 11.4 (1H, br.s, NH); 11.6 (1H, br.s, OH). Found (%): C, 43.1; H, 4.9; N, 18.1. Calculated (%): C, 43.6; H, 5.0; N, 18.2.

16: N-(5-Chloro-1,3-dimethylpyrazolyl-4-methyleneamino)-N'-hydroxyguanidine tosylate (PR20)

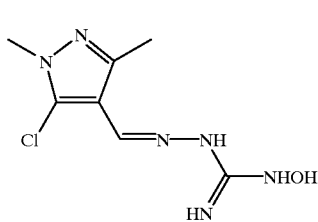

Yield: 62%, m.p. 155–157° C. NMR δ(270 MHz, DMSO): 2.28 (3H, s, CH$_3$); 2.34 (3H, s, CH$_3$); 2.72 (3H, s, CH$_3$); 6.36 (1H, t, C$_4$HN); 7.09 (2H, d, C$_6$H$_2$); 7.49 (2H, d, C$_6$H$_2$); 7.85 (2H, s, NH$_2$); 8.14 (1H, s, CH); 10.1 (1H, br.s, NH); 11.2 (1H, br.s, NH); 11.4 (1H, br.s, OH). Found (%): C, 41.7; H, 4.7; N, 20.9. Calculated (%): C, 41.7; H, 4.8; N, 20.9.

17: N-(Phenylethynylmethyleneamino)-N'-hydroxyguanidine tosylate (PR21)

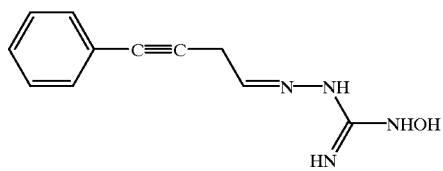

Yield: 42%, m.p. 144–146° C. NMR δ(270 MHz, DMSO): 2.28 (3H, s, CH$_3$); 7.09 (2H, d, C$_6$H$_2$); 7.38÷7.87 (7H, m, C$_6$H$_5$ and C$_6$H$_2$); 8.18 (1H, s, CH); 8.47 (2H, s, NH$_2$); 10.2 (1H, br.s, NH); 11.4 (2H, br.s, NH,OH). Found (%): C, 54.6; H, 4.7; N, 15.0. Calculated (%): C, 54.5; H, 4.8; N, 15.0.

18: N-(3-Bromo-4-methoxybenzylideneamino)-N'-hydroxyguanidine tosylate (EN10)

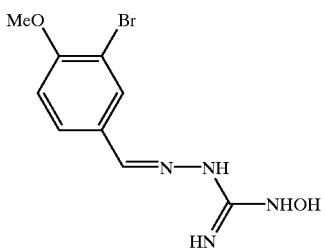

Yield: 31%, m.p. 135–137° C. NMR δ(270 MHz, DMSO): 2.28 (3H, s, CH$_3$); 3.88 (3H, s, CH$_3$); 7.14 (2H, d, C$_6$H$_2$); 7.15 (1H, d, C$_6$H); 7.52 (2H, d, C$_6$H$_2$); 7.72 (1H, dd, C$_6$H); 8.12 (1H, s, CH); 8.20 (2H, s, NH$_2$); 8.29 (1H, d, C$_6$H); 8.55 (1H, br.s, NH); 11.1 (1H, br.s, NH); 11.7 (1H, br,s. OH). Found (%): C, 41.5; H, 4.2; N, 12.2. Calculated (%): C, 41.8; H, 4.4; N, 11.8.

19: N-(4-Trifluoromethylbenzylideneamino)-N'-hydroxyguanidine tosylate (EN12)

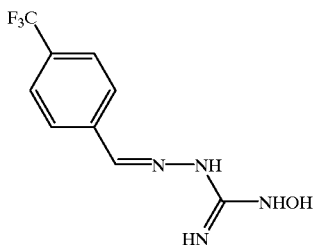

Yield: 56%, m.p. 215–216° C. NMR δ(270 MHz, DMSO): 2.27 (3H, s, CH$_3$); 7.14 (2H, d, C$_6$H$_2$); 7.54 (2H, d, C$_6$H$_2$); 7.77 (2H, d, C$_6$H$_2$); 8.08 (2H, d, C$_6$H$_2$); 8.27 (1H, s, CH); 8.29 (2H, s, NH2); 11.3 (1H, br.s, NH); 12.0 (2H, br.s, NH,OH). Found (%): C, 45.4; H, 4.5; N, 13.4. Calculated (%): C, 45.9; H, 4.1; N, 13.4.

20: N-(3-Phenylpropenyleneamino)-N'-hydroxyguanidine tosylate (EN16)

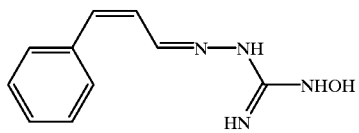

Yield: 39%, m.p. 170–171° C. NMR δ(270 MHz, DMSO): 2.27 (3H, s, CH$_3$); 6.86÷7.00 (1H, m, CH); 7.02÷7.22 (3H, m, CH and C$_6$H$_2$); 7.30÷7.58 (7H, m, C$_6$H$_5$ and C$_6$H$_2$); 8.04 (1H, d, CH); 8.10 (2H, s, NH$_2$); 10.1 (1H, br.s, NH); 11.1 (1H, br.s, NH); 11.7 (1H, br.s, OH). Found (%): C, 53.9; H, 5.2; N, 14.3. Calculated (%): C, 54.2; H, 5.4; N, 14.9.

21: N-(3-Methyl-3-phenylpropyleneamino)-N'-hydroxyguanidine tosylate (EN20)

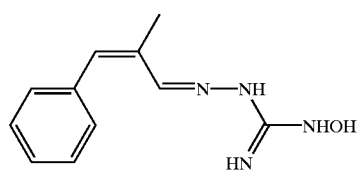

Yield: 41%, m.p. 134–135° C. NMR δ(270 MHz, DMSO): 2.13 (3H, s, CH$_3$); 2.28 (3H, s, CH$_3$); 6.85 (1H, s, CH); 7.15 (2H, d, C$_6$H$_2$); 7.26÷7.50 (5H, m, C$_6$H$_5$); 7.55 (2H, d, C$_6$H$_2$); 8.00 (1H, s, CH); 8.09 (2H, s, NH$_2$); 10.1 (1H, br.s, NH); 11.0 (1H, br.s, NH); 11.7 (1H, br.s, OH). Found (%): C, 55.1; H, 5.9; N, 14.1. Calculated (%): C, 55.4; H, 5.7; N, 14.4.

22: N-(6-Chloro-7-methyl-4oxo-4H-1-benzopyran-3-methyleneamino)-N'-hydroxyguanidine tosylate (EN18)

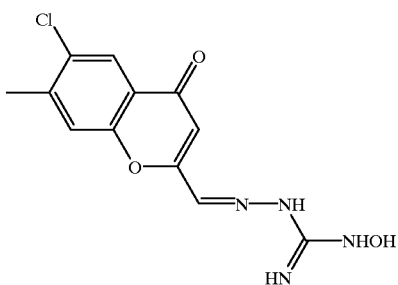

Yield: 43%, m.p. 228–229° C. NMR δ(270 MHz, DMSO): 2.28 (3H, s, CH$_3$); 2.40 (3H, s, Ch$_3$); 7.14 (2H, d, C$_6$H$_2$); 7.53 (2H, d, C$_6$H$_2$); 7.67 (1H, s, C$_6$H); 7.87 (1H, s, C$_6$H); 8.26 (3H, s, CH,NH$_2$); 10.2 (1H, br.s, NH); 11.1 (1H, br.s, NH); 11.9 (1H, br.s, OH). Found (%): C, 48.8; H, 4.4; N, 11.5. Calculated (%): C, 84.9; H, 4.1; N, 12.0.

23: 3-Hydroxyimino-1,2,4-triazole tosylate (PR6)

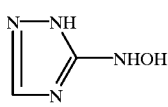

A solution of N-hydroxy-N'-aminoguanidine tosylate (0.66 g; 2.5 mMol) in triethyl orthoformate (1.5 mL) in the presence of boron trifuloride etherate (10 mg) was stirred at room temperature during 8 h. The residue was filtered off and the product crystallised from the ethanol.

Yield 0.32 g (47%), m.p. 188–190° C. NMR δ(270 MHz, DMSO): 2.31 (3H, s, CH$_3$); 7.16 (2H, d, C$_6$H$_2$); 7.53 (2H, d, C$_6$H$_2$); 8.42 (2H, s, NH,NH); 8.78 (1H, s, CH); 11.9 (1H, s, OH). Found (%): C, 39.5; H, 4.4; N, 20.6. Calculated (%): C, 39.7; H, 4.4; N, 20.6.

References: Adamson, R H. *Nature* 1972, 236, 400–401. Amaya, Y et al. *J. Biol Chem.* 1990, 265, 14170–5. Bailey, D M et al. *J. Med. Chem.* 1973, 16, 151–156. Buettner, G R et al. *Free Rad. Biol. Med.* 1991, 11, 69–70. Britigan, B E et al. *J. Biol. Chem.* 1990, 265, 17533–17538. Castelli, P et al. *J Cardiovasc Pharmacol.* 1995, 25, 119–125. Chow, C W et al. *Nucleic Acid Res.* 1994, 22, 1846–54. Clough-Helman, C et al. *Free Radic Res Commun.* 1991, 15, 177–186. Closa, D et al, *Arch Int Physiol Biochim Biophys,* 1994, 102, 167–170. Coghlan, J G et al. *J Thorac Cardiovasc Surg.* 1994, 107, 248–256. Doubell, P C J & D W Oliver. *Drug Res.* 1992, 42, 65–69. Goodman, L S & A. Gilman: *The pharmacological basis of therapeutics.* 4th Ed. Macmillan, London, 1970. Hille, R & T Nishino, FASEB J. 1995, 9, 995–1003. Hui, M B et al. *Antiviral Res.* 1994, 24, 261–273. Ichida, K, S et al. *Gene.* 1993, 133, 279–284. Koneru, PB, et al. *Pharm. Res.* 1993, 10, 515–520. Laemmli, U K. *Nature* (Lond.). 1970, 227, 680-385. Lin, Y & J W Phillis, *Brain Res.* 1992, 571, 272–280. Lowry, O H et al. *J. Biol. Chem.* 1951, 193, 265–275. Mao, G D, et al. *J Biol Chem.* 1993, 268, 416–420. Massey, V et al. *J. Biol. Chem.* 1969, 244, 1682–1691. McCord, J M. *N. Eng. J. Med.* 1985, 312, 159–163. Misawa, M & H Arai. *Agents Actions.* 1993, 38, 19–26. Moriwaki, Y, S et a. *Biochim Biophys Acta.* 1993, 1164, 327–330. Nishino, T. *J. Biochem* (Tokyo). 1994, 116, 1–6. Pfeffer, K D. *J Immunol.* 1994, 153, 1789–1797. Phillis, J W et al. *Neurosci Lett.* 1994, 169, 188–190. Phillis, J W & C Clough-Heffman. *Neurosci Lett.* 1990, 116, 315–319. Pritsos, C A & D L Gustafson. *Oncol Res.* 1994, 6, 477–481. Radak, Z, S et al. *J Appl Physiol.* 1995, 79, 129–135. Russell, G A & R W Cooke, *Arch Dis Child Fetal Neonatal Ed.* 1995, 73, F27–31. Sakai, M, S et al. *Pharmacol Toxicol.* 1995, 77, 36–40. Salim, A S. *J Surg Res.* 1994, 56, 45–52. Saugstad, O D. *Pediatrics.* 1996, 98, 103–107. Singh, N & S Aggarwal. *Int. J Cancer.* 1995, 62, 107–114. Tai, A W et al. *J Med Chem.* 1984, 27, 236–238. T'ang, A et al. *J. Med Chem.* 1985, 28, 1103–1106. Uhlén, S & J E S Wikberg. *Eur J Pharmacol.* 1991, 202, 235–243. Wajner, M & R A Harkness. *Biochem Biophys Acta.* 1989, 991, 79–84. Wakabayashi, Y, S et al. *Biochim Biophys Acta.* 1995, 1265, 103–109. Walker, J H & M S Walker. *J. Biol Chem.* 1959, 234, 1481–1484. Wang, P-H et al. *J Med Chem.* 1990, 22, 608–614. Weckbecker, G S et al. *Cancer Res.* 1987, 47, 975–978. Weckbecker, G S et al. *J Natl Cancer Inst.* 1988, 80, 491–496. Wiezorek, J S et al. *J Clin Invest.* 1994, 94, 2224–2230. Wright, R M et al, *Proc Natl Acad Sci USA.* 1993, 90, 10690–10694. Xia, Y et al. *J Biol Chem.* 1996, 271, 10096–10102.

What is claimed is:

1. A pharmaceutical composition comprising a pharmaceutically acceptable carrier and a hydroxyguanidine, wherein the hydroxyguanidine has the formula (1)

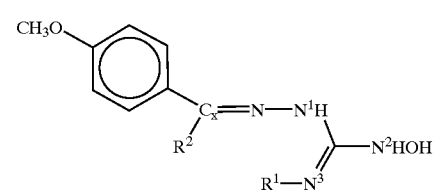

(1)

(1) wherein the 4-methoxyphenyl group may be optionally further substituted; and (2) wherein $R^1$ is selected from the group consisting of: H, alkyl, alkenyl, cycloalkyl, cycloalkenyl, cycloheteroalkyl, cycloheteroalkenyl, alkynyl, aryl, heteroaryl, or
 (A) wherein $R^1$ or $R^2$ is a carbon atom or heteroatom which taken together with $R^2$ or $R^1$ forms a 6-membered ring structure; or (3) wherein $R^2$ is selected from the group consisting of: H, alkyl, alkenyl, cycloalkyl, cycloalkenyl, cycloheteroalkyl, cycloheteroalkenyl, alkynyl, aryl, heteroaryl; and (4) wherein any of the 5- or 6-membered ring structures may optionally be fused with cycloalkyl, cycloheteroalkyl, cycloalkenyl, cycloheteroalkenyl, aryl or heteroaryl.

2. A pharmaceutical composition comprising a pharmaceutically acceptable carrier and a hydroxyguanidine, wherein the hydroxyguanidine has the formula (1)

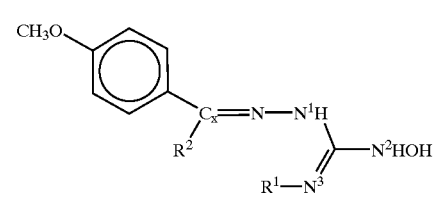

(1)

(1) wherein $R^1$ is selected from the group consisting of: H, alkyl, alkenyl, cycloalkyl, cycloalkenyl, cycloheteroalkyl, cycloheteroalkenyl, alkynyl, aryl, heteroaryl, or
 (A) wherein $R^1$ or $R^2$ is a carbon atom or heteroatom which taken together with $R^2$ or $R^1$ forms a cyclic or heterocyclic structure; or
 (B) wherein $R^1$ and $R^2$ are a single bond between $N^3$ and $C_{x}$; or (2) wherein $R^2$ is selected from the group consisting of: H, alkyl, alkenyl, cycloalkyl, cycloalkenyl, cycloheteroalkyl, cycloheteroalkenyl, alkynyl, aryl, heteroaryl; and (3) wherein at least one hydrogen in $R^1$ or $R^2$ is independently substituted with alkyl, alkenyl, cycloalkyl, cycloheteroalkyl, cycloalkenyl, cycloheteroalkenyl, alkynyl, aryl, or heteroaryl.

3. The composition of claim 2, wherein at least one hydrogen in any of said alkyls, alkenyls, cycloalkyls, cycloheteroalkyls, cycloalkenyls, cycloheteroalkenyls, alkynyls, aryls, heteroaryls, or functional groups is independently substituted with a halogen or a functional group.

4. A pharmaceutical composition comprising a pharmaceutically acceptable carrier and a hydroxyguanidine selected from the group consisting of: LW01, LW04, PR1, PR2, PR4, PR6, PR8, PR10, PR11, PR12, PR13, PR14, PR15, PR16, PR17, PR18, PR19, PR20, PR21, EN16, and EN20.

5. A pharmaceutical composition comprising a hydroxyguanidine, a pharmaceutically acceptable carrier and a xanthine dehydrogenase and/or xanthine oxidase blocking drug.

6. The composition of claim 5, wherein the xanthine dehydrogenase and/or xanthine oxidase blocking drug is selected from the group consisting of: allopurinol, oxypurinol and amflutizole.

7. A pharmaceutical composition comprising a hydroxyguanidine, a pharmaceutically acceptable carrier and at least one compound selected from the group consisting of: a radical scavenger, adenosine deaminase inhibitor, superoxide dismutase and superoxide dismutase mimetic.

8. The composition of claim 7, wherein the compound is selected from the group of: EHNA (erythro-9-(2-hydroxy-3-nonyl)adenine),DCF (2'-deoxycoformycin), catalase, vitamin E(alpha-tocopherol), vitamin C, glutathione, uric acid, N-tert-butyl-alpha-phenynitrone (PBN), dimethylsulfoxide (DMSO), N-acetyl-cysteine (NAC), dimethylthiourea (DMU) and beta-carotens.

9. A pharmaceutical composition comprising a hydroxyguanidine wherein the hydroxyguanidine has the formula:

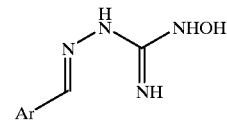

wherein Ar is a 4-methoxyphenyl group optionally subtituted with one or more functional groups.

10. The pharmaceutical composition of claim 9, wherein Ar is a 4 methoxyphenyl group.

11. The pharmaceutical composition of claim 9, wherein the hydroxyguanidine is selected from the group consisting of DW01, DW02, DW03, DW04, DW05, DW06, DW07, DW08, and EN10.

12. The pharmaceutical composition of claim 9, wherein the hydroxyguanidine is PR5.

* * * * *